(12) United States Patent
Moerck et al.

(10) Patent No.: US 7,588,782 B2
(45) Date of Patent: *Sep. 15, 2009

(54) RARE EARTH METAL COMPOSITIONS FOR TREATING HYPERPHOSPHATEMIA AND RELATED METHODS

(75) Inventors: Rudi E. Moerck, San Antonio, TX (US); Timothy Malcome Spitler, Fernley, NV (US); Edward A. Schauer, Sparks, NV (US); Jan Prochazka, Reno, NV (US)

(73) Assignee: Altairnano, Inc., Reno, NV (US)

( * ) Notice: Subject to any disclaimer, the term of this patent is extended or adjusted under 35 U.S.C. 154(b) by 397 days.

This patent is subject to a terminal disclaimer.

(21) Appl. No.: 11/181,650

(22) Filed: Jul. 13, 2005

(65) Prior Publication Data

US 2006/0003018 A1    Jan. 5, 2006

Related U.S. Application Data

(63) Continuation of application No. 10/444,774, filed on May 23, 2003, now abandoned.

(60) Provisional application No. 60/461,175, filed on Apr. 8, 2003, provisional application No. 60/430,284, filed on Dec. 2, 2002, provisional application No. 60/403,868, filed on Aug. 14, 2002, provisional application No. 60/396,989, filed on May 24, 2002.

(51) Int. Cl.
*A61K 33/24* (2006.01)
*A61K 9/14* (2006.01)
*A61P 3/00* (2006.01)

(52) U.S. Cl. .................................. 424/617; 424/489

(58) Field of Classification Search ................ 424/617, 424/489

See application file for complete search history.

(56) References Cited

U.S. PATENT DOCUMENTS

| | | | |
|---|---|---|---|
| 3,692,671 A | 9/1972 | Recht et al. | |
| 3,768,989 A | 10/1973 | Goetzinger et al. | |
| 3,922,331 A | 11/1975 | MacDonald et al. | |
| 3,922,333 A | 11/1975 | Mazdiyasni et al. | |
| 4,454,162 A | 6/1984 | Schanze et al. | |
| 4,462,970 A | 7/1984 | Pastor et al. | |
| 4,929,787 A | 5/1990 | Cameron et al. | |
| 5,407,560 A | 4/1995 | Miyawaki et al. | |
| 5,539,000 A | 7/1996 | Leonard | |
| 5,683,953 A | 11/1997 | Mills | |
| 5,782,792 A | 7/1998 | Jones et al. | |
| 5,843,477 A | 12/1998 | Alexander | |
| 5,968,976 A | 10/1999 | Murrer et al. | |
| 6,146,539 A | 11/2000 | Mills | |
| 6,197,201 B1 | 3/2001 | Misra et al. | |
| 6,312,604 B1 | 11/2001 | Denkewicz, Jr. et al. | |
| 6,322,895 B1 | 11/2001 | Canham | |
| 6,338,800 B1 | 1/2002 | Kulperger et al. | |
| 6,521,647 B2 | 2/2003 | Foster | |
| 6,849,609 B2 | 2/2005 | Morrison | |
| 6,858,203 B2 | 2/2005 | Holmes-Farley et al. | |
| 7,078,059 B2 * | 7/2006 | Atherton et al. ............. | 424/617 |
| 7,119,120 B2 | 10/2006 | Jozefiak et al. | |
| 7,381,428 B2 * | 6/2008 | Ferdinando et al. ......... | 424/715 |
| 7,465,465 B2 * | 12/2008 | Haslam et al. ............... | 424/600 |
| 2003/0235616 A1 | 12/2003 | Sowden et al. | |
| 2004/0161474 A1 | 8/2004 | Moerck et al. | |
| 2005/0131138 A1 | 6/2005 | Connor et al. | |
| 2005/0247628 A1 | 11/2005 | Moerck et al. | |
| 2006/0002837 A1 | 1/2006 | Moerck et al. | |
| 2006/0083791 A1 | 4/2006 | Moerck et al. | |
| 2006/0134225 A1 | 6/2006 | Moerck et al. | |
| 2006/0153932 A1 * | 7/2006 | Ferdinando et al. ......... | 424/617 |
| 2007/0149405 A1 | 6/2007 | Spitler | |
| 2008/0058250 A1 | 3/2008 | Wren et al. | |
| 2008/0069860 A1 | 3/2008 | Wren et al. | |

FOREIGN PATENT DOCUMENTS

| | | |
|---|---|---|
| EP | 0604919 A1 | 7/1994 |
| JP | 61004529 A2 | 1/1986 |
| JP | 0810610 A | 1/1996 |
| WO | WO-96/30029 A1 | 10/1996 |
| WO | WO 99/15189 A1 | 4/1999 |
| WO | WO 02/22258 A2 | 3/2002 |
| WO | WO-02/060818 A1 | 8/2002 |
| WO | WO-03/094933 A2 | 11/2002 |

OTHER PUBLICATIONS

Medline abstract 86308884 (1986).*
Yamaguchi et al., Abstract for "Formation and Decomposition of Lanthanum Monoxocarbonate," Zeitschrift fuer Anorganiche und Allgemeine Chemie, 514, 1984, pp. 205-212, obtained from Chemabs "Online", Chemical Abstracts Service, Columbus OH; 1 pg.
Holsa et al., Abstract for "Preparation, Thermal Stability and Luminescence Properties of Selected Rare Earth Oxycarbonates," Thermochimica Acta, 190(2), pp. 335-343, 1991, Chemabs "Online", Chemical Abstracts Service, Columbus, OH; 1 pg.
Graff et al., "A Possible Non-Aluminum Oral Phosphate Binder? A Comparative Study on Dietary Phosphorus Absorption," Research Communications in Molecular Pathology and Pharmacology, vol. 89, No. 3, Sep. 1995, pp. 373-388.
Olafsen et al., Abstract for "Synthesis of Rare Earth Oxide Carbonates and Thermal Stability of Nd2O2C03 II," Journal of Materials Chemistry, 9(10), 1999, pp. 2697-2702, obtained from Database Chemabs "Online," Chemical Abstracts Service, Columbus, OH, 1 pg.

(Continued)

*Primary Examiner*—John Pak
(74) *Attorney, Agent, or Firm*—Dillon & Yudell LLP

(57) ABSTRACT

Rare earth metal compounds, particularly lanthanum, cerium, and yttrium, are formed as porous particles and are effective in binding metals, metal ions, and phosphate. A method of making the particles and a method of using the particles is disclosed. The particles may be used in the gastrointestinal tract or the bloodstream to remove phosphate or to treat hyperphosphatemia in mammals. The particles may also be used to remove metals from fluids such as water.

12 Claims, 29 Drawing Sheets

OTHER PUBLICATIONS

Finn et al., "Results of a Randomized Dose-Ranging, Placebo Controlled Study of Lanthanum Carbonate for Reduction of Serum Phosphate in Chronic Renal Failure Patients Receiving Hemodialysis," Journal of the American Society of Nephrology, Miami, FL; Nov. 1999.

Behets et al., "An Assessment of the Effects of Lanthanum on Bone in a Chronic Renal Failure (CFR) Rat Model," Journal of the American Society of Nephrology, Miami, FL; Nov. 1999.

Joy et al., "Safety Profile of Lanthanum Carbonate in Hemodialysis Patients: Results From a Phase III U.S. Study," Journal of the American Society of Nephrology, Miami, FL; Nov. 1999.

Behets et al., "Effects of the Phosphate Binder Renagel® (Sevelamer) on Biochemical Parameters and Bone Histology in a Chronic Renal Failure (CRF) Rat Model," Journal of the American Society of Nephrology, Miami, FL; Nov. 1999.

Joy et al., "Results of Randomized, Phase III, Dose-Titration, Parallel Group Study of Lanthanum Carbonate for Reduction and Maintenance of Serum Phosphate in Chronic Hemodialysis Patients," Journal of the American Society of Nephrology, Miami, FL; Nov. 1999.

DeBroe et al., "Lanthanum Carbonate (Fosrenol™), A New Agent in the Treatment of Hyperphosphatemia in End-State Renal Failure," University Hospital of Antwerp, Belgium, 2002.

Shire Pharmaceutical Development Ltd., Programme for "New Directions in the Treatment of Hyperphosphatemia," European Renal Association Conference, Jul. 14, 2002, Copenhagen, Denmark.

Damment et al., "Bone Mineralisation Defect with High Doses of Phosphate Binders in Uraemic Rats—An Artefact of Phosphate Depletion?," European Renal Association Conference, Jul. 14, 2002, Copenhagen, Denmark.

Stewart et al., "Administration of a Novel Phosphate Binder, Fosrenol™, with Food Is Associated with Good Tolerability and Low Systemic Absorption," ASN 35th Annual Meeting & Scientific Exposition, Nov. 2002, Philadelphia, PA.

Sack et al., "Fosrenal™ (Lanthanum Carbonate) is Well Tolerated in Patients Requiring Hemodialysis: Results of a Phase I Clinical Trial," ASN 35th Annual Meeting & Scientific Exposition, Nov. 2002, Philadelphia, PA.

Hutchison, A.J., "The Novel, Non-Aluminum, Non-Calcium Phosphate Binder, Lanthanum Carbonate (Fosrenol™), is an Effective Treatment for Hyperphosphatemia and has a Good Safety Profile," ASN 35th Annual Meeting & Scientific Exposition, Nov. 2002, Philadelphia, PA.

Finn et al., "Fosrenol™, a Novel, Non-Calcium, Non-Aluminum Phosphate Binder, Has a Good Safety and Efficacy Profile in the Long-Term Treatment of Hyperphosphatemia in Hemodialysis Patients," ASN 35th Annual Meeting & Scientific Exposition, Nov. 2002.

Finn et al., "Efficacy and Safety of Long-Term Treatment with Lanthanum Carbonate—A Novel Phosphate-Binding Agent," National Kidney Foundation Clinical Meeting, Apr. 2003, Dallas, TX.

D'Haese et al., "The Effects of Lanthanum Carbonate (Fosrenol™) and Calcium Carbonate on Renal Bone Disease in Dialysis Patients," National Kidney Foundation Clinical Meeting, Apr. 2003, Dallas, TX.

Hutchison et al., "Safety and Efficacy of Lanthanum Carbonate for Treatment of Hyperphosphatemia in Haemodialysis Patients over 12 months," National Kidney Foundation Clinical Meeting, Apr. 2003, Dallas, TX.

Fiddler et al., "Lanthanum Carbonate has a good Safety Profile Following Concomitant Administration with Metropol and Has No Clinically Significant Effect on its Pharmacokinetics," National Kidney Foundation Clinical Meeting, Apr. 2003, Dallas, TX.

Fiddler et al., "Lanthanum Carbonate Has No Effect on the Pharmacokinetics of Digoxin and Can be Administered Safely in Combination," National Kidney Foundation Clinical Meeting, Apr. 2003, Dallas, TX.

Fiddler et al., "Lanthanum Carbonate is Well Tolerated When Administered with Warfarin and Has No Effect on its Pharmacokinetics," National Kidney Foundation Clinical Meeting, Apr. 2003, Dallas, TX.

Hutchinson et al., "Safety, Tolerability and Efficacy of Lanthanum Carbonate in Haemodialysis Patients: a 12-Month Study," ERA-EDTA World Congress of Nephrology, Jun. 2003, Berlin, Germany.

*Dictionary of Chemistry and Chemical Technology*. (1999). p. 2240-2242. (English translation attached, 13 pages).

European Search Report mailed Aug. 16, 2006, for EP 06000002.3 filed Aug. 8, 2003, 10 pages.

International Preliminary Examination Report mailed Jan. 3, 2005, PCT Application No. PCT/US03/25192 filed Aug. 8, 2003, 7 pages.

International Search Report and Written Opinion mailed Jul. 20, 2007, for PCT Application No. PCT/US06/32415 filed Aug. 17, 2006, 8 pages.

International Search Report and Written Opinion mailed Jun. 3, 2008, for PCT Application No. PCT/US06/32492 filed Aug. 17, 2006, 8 pages.

International Search Report and Written Opinion mailed Mar. 21, 2008, for PCT Application No. PCT/US05/37015 filed Oct. 13, 2005, 16 pages.

International Search Report mailed Jun. 1, 2004, for PCT Application No. PCT/US03/38235 filed Dec. 2, 2003, 6 pages.

International Search Report mailed Jun. 7, 2004, for PCT Application No. PCT/US03/25192 filed Aug. 8, 2003, 11 pages.

International Written Opinion mailed Mar. 21, 2005, PCT Application No. PCT/US03/38235 filed Dec. 2, 2003, 5 pages.

Joy, M. S. et al. (2003). "Randomized, Double-Blind, Placebo-Controlled, Dose Titration, Phase III Study Assessing Efficacy and Tolerability of Lanthanum Carbonate: A New Phosphate Binder for the Treatment of Hyperphosphatemia," *American Journal of Kidney Diseases* 42:96-107. (Abstract only obtained from Chemical Abstracts HCAplus, 2003:602063, 1 page).

Nagashima, K. et al. (Jan. 1973). "The Synthesis of Crystalline Rare Earth Carbonates," *Bulletin of the Chemical Society of Japan* 46(1):152-156.

Olafsen, A. et al. (2001). "On the Crystal Structure of $Ln_2O_2CO_3$ II (Ln=La and Nd)," *Journal of Solid State Chemistry* 158:14-24 (Abstract only obtained from Chemical Abstracts HCAplus, 2001:260955, 1 pages).

Partial European Search Report mailed Apr. 18, 2006, for EP 06000002.3 filed Aug. 8, 2003, 7 pages.

Rudnic, E. R. et al. (1990). "Oral Solid Dosage Forms," Chapter 89 *In Remington: Pharmaceutical Sciences*. 18th Edition, pp. 1633-1658.

U.S. Office Action mailed Dec. 4, 2007, for U.S. Appl. No. 10/444,774, filed May 23, 2003, 9 pages.

U.S. Office Action mailed Feb. 16, 2006, for U.S. Appl. No. 10/444,774, filed May 23, 2003, 7 pages.

U.S. Office Action mailed May 25, 2007, for U.S. Appl. No. 10/444,774, filed May 23, 2003, 10 pages.

U.S. Office Action mailed Sep. 17, 2008, for U.S. Appl. No. 11/181,609, filed Jul. 13, 2005, 6 pages.

U.S. Office Action mailed Sep. 8, 2006, for U.S. Appl. No. 10/444,774, filed May 23, 2003, 8 pages.

U.S. Appl. No. 11/576,785, filed Apr. 5, 2007 for Moerck et al.

U.S. Appl. No. 12/051,726, filed Mar. 19, 2008 for Moerck et al.

U.S. Appl. No. 12/197,157, filed Aug. 22, 2008 for Moerck et al.

\* cited by examiner x, the number of water molecules in the compound, is larger or equal to 2 and smaller or equal to 4.

RARE EARTH METAL COMPOSITIONS FOR TREATING HYPERPHOSPHATEMIA AND RELATED METHODS

This application is a Continuation of U.S. application Ser. No. 10/444,774, filed May 23, 2003, now abandoned, which claims benefit of priority to U.S. Provisional Application No. 60/396,989, filed May 24, 2002, U.S. Provisional Application No. 60/403,868, filed Aug. 14, 2002, U.S. Provisional Application No. 60/430,284, filed Dec. 2, 2002, and U.S. Provisional Application No. 60/461,175, filed Apr. 8, 2003, and the entire contents of each is hereby incorporated by reference.

The present invention relates to rare earth metal compounds, particularly rare earth metal compounds having a porous structure. The present invention also includes methods of making the porous rare earth metal compounds and methods of using the compounds of the present invention. The compounds of the present invention can be used to bind or absorb metals such as arsenic, selenium, antimony and metal ions such as arsenic $III^+$ and $V^+$. The compounds of the present invention may therefore find use in water filters or other devices or methods to remove metals and metal ions from fluids, especially water.

The compounds of the present invention are also useful for binding or absorbing anions such as phosphate in the gastrointestinal tract of mammals. Accordingly, one use of the compounds of the present invention is to treat high serum phosphate levels in patients with end-stage renal disease undergoing kidney dialysis. In this aspect, the compounds may be provided in a filter that is fluidically connected with a kidney dialysis machine such that the phosphate content in the blood is reduced after passing through the filter.

In another aspect, the compounds can be used to deliver a lanthanum or other rare-earth metal compound that will bind phosphate present in the gut and prevent its transfer into the bloodstream. Compounds of the present invention can also be used to deliver drugs or to act as a filter or absorber in the gastrointestinal tract or in the blood stream. For example, the materials can be used to deliver inorganic chemicals in the gastrointestinal tract or elsewhere.

It has been found that the porous particle structure and the high surface area are beneficial to high absorption rates of anions. Advantageously, these properties permit the compounds of the present invention to be used to bind phosphate directly in a filtering device fluidically connected with kidney dialysis equipment.

The use of rare earth hydrated oxides, particularly hydrated oxides of La, Ce, and Y to bind phosphate is disclosed in Japanese published patent application 61-004529 (1986). Similarly, U.S. Pat. No. 5,968,976 discloses a lanthanum carbonate hydrate to remove phosphate in the gastrointestinal tract and to treat hyperphosphatemia in patients with renal failure. It also shows that hydrated lanthanum carbonates with about 3 to 6 molecules of crystal water provide the highest removal rates. U.S. Pat. No. 6,322,895 discloses a form of silicon with micron-sized or nano-sized pores that can be used to release drugs slowly in the body. U.S. Pat. No. 5,782,792 discloses a method for the treatment of rheumatic arthritis where a "protein A immunoadsorbent" is placed on silica or another inert binder in a cartridge to physically remove antibodies from the bloodstream.

It has now unexpectedly been found that the specific surface area of compounds according to the present invention as measured by the BET method, varies depending on the method of preparation, and has a significant effect on the properties of the product. As a result, the specific properties of the resulting compound can be adjusted by varying one or more parameters in the method of making the compound. In this regard, the compounds of the present invention have a BET specific surface area of at least about 10 $m^2/g$ and may have a BET specific surface area of at least about 20 $m^2/g$ and alternatively may have a BET specific surface area of at least about 35 $m^2/g$. In one embodiment, the compounds have a BET specific surface area within the range of about 10 $m^2/g$ and about 40 $m^2/g$.

It has also been found that modifications in the preparation method of the rare earth compounds will create different entities, e.g. different kinds of hydrated or amorphous oxycarbonates rather than carbonates, and that these compounds have distinct and improved properties. It has also been found that modifications of the preparation method create different porous physical structures with improved properties.

The compounds of the present invention and in particular, the lanthanum compounds and more particularly the lanthanum oxycarbonates of the present invention exhibit phosphate binding or removal of at least 40% of the initial concentration of phosphate after ten minutes. Desirably, the lanthanum compounds exhibit phosphate binding or removal of at least 60% of the initial concentration of phosphate after ten minutes. In other words, the lanthanum compounds and in particular, the lanthanum compounds and more particularly the lanthanum oxycarbonates of the present invention exhibit a phosphate binding capacity of at least 45 mg of phosphate per gram of lanthanum compound. Suitably, the lanthanum compounds exhibit a phosphate binding capacity of at least 50 mg $PO_4$/g of lanthanum compound, more suitably, a phosphate binding capacity of at least 75 mg $PO_4$/g of lanthanum compound. Desirably, the lanthanum compounds exhibit a phosphate binding capacity of at least 100 mg $PO_4$/g of lanthanum compound, more desirably, a phosphate binding capacity of at least 110 mg $PO_4$/g of lanthanum compound.

In accordance with the present invention, rare earth metal compounds, and in particular, rare earth metal oxychlorides and oxycarbonates are provided. The oxycarbonates may be hydrated or anhydrous. These compounds may be produced according to the present invention as particles having a porous structure. The rare earth metal compound particles of the present invention may conveniently be produced within a controllable range of surface areas with resultant variable and controllable adsorption rates of ions.

The porous particles or porous structures of the present invention are made of nano-sized to micron-sized crystals with controllable surface areas. The rare earth oxychloride is desirably lanthanum oxychloride (LaOCl). The rare earth oxycarbonate hydrate is desirably lanthanum oxycarbonate hydrate ($La_2O(CO_3)_2 \cdot xH_2O$ where x is from and including 2 to and including 4). This compound will further be referred to in this text as $La_2O(CO_3)_2 \cdot xH_2O$. The anhydrous rare earth oxycarbonate is desirably lanthanum oxycarbonate $La_2O_2CO_3$ or $La_2CO_5$ of which several crystalline forms exist. The lower temperature form will be identified as $La_2O_2CO_3$ and the form obtained at higher temperature or after a longer calcination time will be identified as $La_2CO_5$.

One skilled in the art, however, will understand that lanthanum oxycarbonate may be present as a mixture of the hydrate and the anhydrous form. In addition, the anhydrous lanthanum oxycarbonate may be present as a mixture of $La_2O_2CO_3$ and $La_2CO_5$ and may be present in more than a single crystalline form.

One method of making the rare earth metal compound particles includes making a solution of rare earth metal chloride, subjecting the solution to a substantially total evaporation process using a spray dryer or other suitable equipment to form an intermediate product, and calcining the obtained intermediate product at a temperature between about 500° and about 1200° C. The product of the calcination step may be washed, filtered, and dried to make a suitable finished product. Optionally, the intermediate product may be milled in a horizontal or vertical pressure media mill to a desired surface area and then further spray dried or dried by other means to produce a powder that may be further washed and filtered.

An alternative method of making the rare earth metal compounds, particularly rare earth metal anhydrous oxycarbonate particles includes making a solution of rare earth metal acetate, subjecting the solution to a substantially total evaporation process using a spray dryer or other suitable equipment to make an intermediate product, and calcining the obtained intermediate product at a temperature between about 400° C. and about 700° C. The product of the calcination step may be washed, filtered, and dried to make a suitable finished product. Optionally, the intermediate product may be milled in a horizontal or vertical pressure media mill to a desired surface area, spray dried or dried by other means to produce a powder that may be washed, filtered, and dried.

Yet another method of making the rare earth metal compounds includes making rare earth metal oxycarbonate hydrate particles. The rare earth metal oxycarbonate hydrate particles can be made by successively making a solution of rare earth chloride, subjecting the solution to a slow, steady feed of a sodium carbonate solution at a temperature between about 30° and about 90° C. while mixing, then filtering and washing the precipitate to form a filter cake, then drying the filter cake at a temperature of about 100° to 120° C. to produce the desired rare earth oxycarbonate hydrate species. Optionally, the filter cake may be sequentially dried, slurried, and milled in a horizontal or vertical pressure media mill to a desired surface area, spray dried or dried by other means to produce a powder that may be washed, filtered, and dried.

Alternatively, the process for making rare earth metal oxycarbonate hydrate particles may be modified to produce anhydrous particles. This modification includes subjecting the dried filter cake to a thermal treatment at a specified temperature between about 400° C. to about 700° C. and for a specified time between 1 h and 48 h. Optionally, the product of the thermal treatment may be slurried and milled in a horizontal or vertical pressure media mill to a desired surface area, spray dried or dried by other means to produce a powder that may be washed, filtered, and dried.

In accordance with the present invention, compounds of the present invention may be used to treat patients with hyperphosphatemia. The compounds may be made into a form that may be delivered to a mammal and that may be used to remove phosphate from the gut or decrease phosphate absorption into the blood stream. For example, the compounds may be formulated to provide an orally ingestible form such as a liquid solution or suspension, a tablet, capsule, gelcap, or other suitable and known oral form. Accordingly, the present invention contemplates a method for treating hyperphosphatemia that comprises providing an effective amount of a compound of the present invention. Compounds made under different conditions will correspond to different oxycarbonates or oxychlorides, will have different surface areas, and will show differences in reaction rates with phosphate and different solubilization of lanthanum or another rare-earth metal into the gut. The present invention allows one to modify these properties according to the requirements of the treatment.

In another aspect of the present invention, compounds made according to this invention as a porous structure of sufficient mechanical strength may be placed in a device fluidically connected to a dialysis machine through which the blood flows, to directly remove phosphate by reaction of the rare-earth compound with phosphate in the bloodstream. The present invention therefore contemplates a device having an inlet and an outlet with one or more compounds of the present invention disposed between the inlet and the outlet. The present invention also contemplates a method of reducing the amount of phosphate in blood that comprises contacting the blood with one or more compounds of the present invention for a time sufficient to reduce the amount of phosphate in the blood.

In yet another aspect of the present invention, the compounds of the present invention may be used as a substrate for a filter having an inlet and outlet such that the compounds of the present invention are disposed between the inlet and the outlet. A fluid containing a metal, metal ion, phosphate or other ion may be passed from the inlet to contact the compounds of the present invention and through the outlet. Accordingly, in one aspect of the present invention a method of reducing the content of a metal in a fluid, for example water, comprises flowing the fluid through a filter that contains one or more compounds of the present invention to reduce the amount of metal present in the water.

DESCRIPTION OF THE INVENTION

Figure 1:
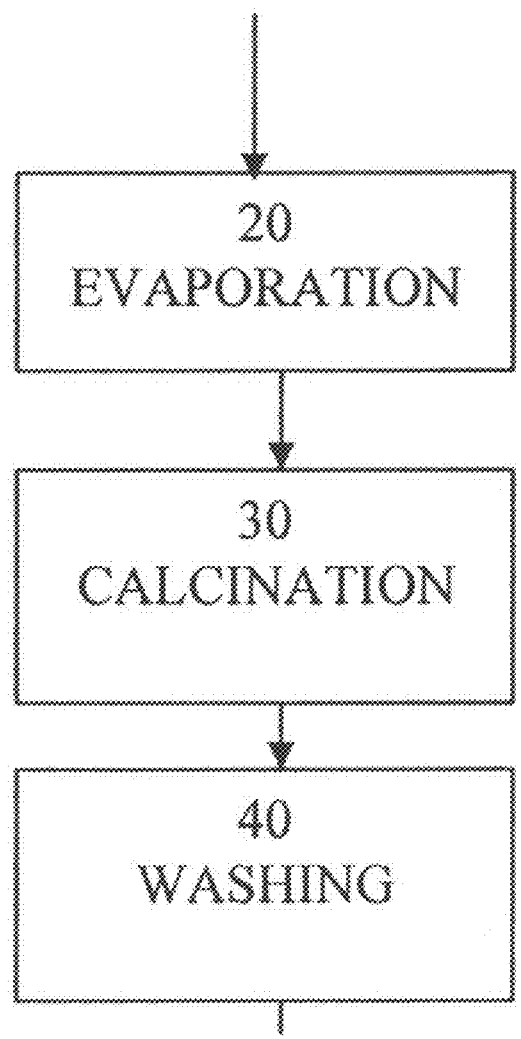
FIG. 1 is a general flow sheet of a process according to the present invention that produces LaOCl (lanthanum oxychloride).

Referring now to the drawings, the process of the present invention will be described. While the description will generally refer to lanthanum compounds, the use of lanthanum is merely for ease of description and is not intended to limit the invention and claims solely to lanthanum compounds. In fact, it is contemplated that the process and the compounds described in the present specification is equally applicable to rare earth metals other than lanthanum such as Ce and Y.

Turning now to FIG. 1, a process for making a rare earth oxychloride compound, and, in particular a lanthanum oxychloride compound according to one embodiment of the present invention is shown. First, a solution of lanthanum chloride is provided. The source of lanthanum chloride may be any suitable source and is not limited to any particular source. One source of lanthanum chloride solution is to dissolve commercial lanthanum chloride crystals in water or in an HCl solution. Another source is to dissolve lanthanum oxide in a hydrochloric acid solution.

The lanthanum chloride solution is evaporated to form an intermediate product. The evaporation 20 is conducted under conditions to achieve substantially total evaporation. Desirably, the evaporation is conducted at a temperature higher than the boiling point of the feed solution (lanthanum chloride) but lower than the temperature where significant crystal growth occurs. The resulting intermediate product may be an amorphous solid formed as a thin film or may have a spherical shape or a shape as part of a sphere.

The terms "substantially total evaporation" or "substantially complete evaporation" as used in the specification and claims refer to evaporation such that the resulting solid intermediate contains less than 15% free water, desirably less than 10% free water, and more desirably less than 1% free water. The term "free water" is understood and means water that is not chemically bound and can be removed by heating at a temperature below 150° C. After substantially total evaporation or substantially complete evaporation, the intermediate product will have no visible moisture present.

The evaporation step may be conducted in a spray dryer. In this case, the intermediate product will consist of a structure of spheres or parts of spheres. The spray dryer generally operates at a discharge temperature between about 120° C. and about 500° C.

The intermediate product may then be calcined in any suitable calcination apparatus 30 by raising the temperature to a temperature between about 500° C. to about 1200° C. for a period of time from about 2 to about 24 h and then cooling to room temperature. The cooled product may be washed 40 by immersing it in water or dilute acid, to remove any water-soluble phase that may still be present after the calcination step 30.

The temperature and the length of time of the calcination process may be varied to adjust the particle size and the reactivity of the product. The particles resulting from calcination generally have a size between 1 and 1000 μm. The calcined particles consist of individual crystals, bound together in a structure with good physical strength and a porous structure. The individual crystals forming the particles generally have a size between 20 nm and 10 μm.

Figure 2:
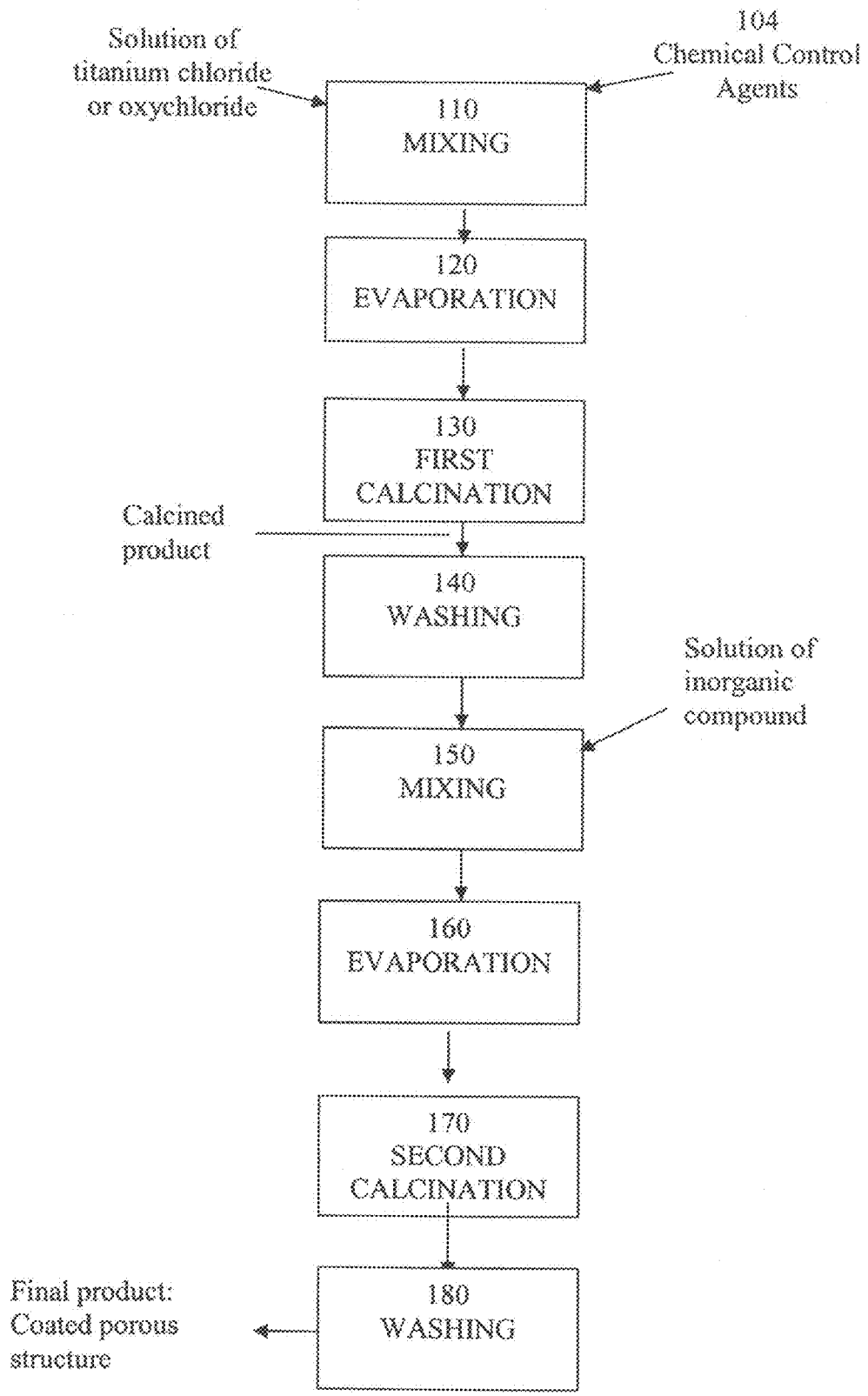
FIG. 2 is a flow sheet of a process according to the present invention that produces a coated titanium dioxide structure.

In accordance with another embodiment of the present invention as shown in FIG. 2, a feed solution of titanium chloride or titanium oxychloride is provided by any suitable source. One source is to dissolve anhydrous titanium chloride in water or in a hydrochloric acid solution. Chemical control agents or additives 104 may be introduced to this feed solution to influence the crystal form and the particle size of the final product. One chemical additive is sodium phosphate $Na_3PO_4$. The feed solution of titanium chloride or titanium oxychloride is mixed with the optional chemical control agent 104 in a suitable mixing step 110. The mixing may be conducted using any suitable known mixer.

The feed solution is evaporated to form an intermediate product, which in this instance is titanium dioxide ($TiO_2$). The evaporation 120 is conducted at a temperature higher than the boiling point of the feed solution but lower than the temperature where significant crystal growth occurs and to achieve substantially total evaporation. The resulting intermediate product may desirably be an amorphous solid formed as a thin film and may have a spherical shape or a shape as part of a sphere.

The intermediate product may then be calcined in any suitable calcination apparatus 130 by raising the temperature to a temperature between about 400° C. to about 1200° C. for a period of time from about 2 to about 24 h and then cooling to room temperature (25° C.). The cooled product is then washed 140 by immersing it in water or dilute acid, to remove traces of any water-soluble phase that may still be present after the calcination step.

The method of manufacture of the intermediate product according to the present invention can be adjusted and chosen to make a structure with the required particle size and porosity. For example, the evaporation step 120 and the calcination step 130 can be adjusted for this purpose. The particle size and porosity can be adjusted to make the structure of the intermediate product suitable to be used as an inert filter in the bloodstream.

The washed $TiO_2$ product is then suspended or slurried in a solution of an inorganic compound. A desirable inorganic compound is a rare-earth or lanthanum compound, and in particular lanthanum chloride. This suspension of $TiO_2$ in the inorganic compound solution is again subjected to total evaporation 160 under conditions in the same range as defined in step 120 and to achieve substantially total evaporation. In this regard, the evaporation steps 120 and 160 may be conducted in a spray drier. The inorganic compound will precipitate as a salt, an oxide, or an oxy-salt. If the inorganic compound is lanthanum chloride, the precipitated product will be lanthanum oxychloride. If the original compound is lanthanum acetate, the precipitated product will be lanthanum oxide.

The product of step 160 is further calcined 170 at a temperature between 500° and 1100° C. for a period of 2 to 24 h. The temperature and the time of the calcination process influence the properties and the particle size of the product. After the second calcination step 170, the product may be washed 180.

The resulting product can be described as crystals of lanthanum oxychloride or lanthanum oxide formed on a $TiO_2$ substrate. The resulting product may be in the form of hollow thin-film spheres or parts of spheres. The spheres will have a size of about 1 μm to 1000 μm and will consist of a structure of individual bound particles. The individual particles have a size between 20 nm and 10 μm.

When the final product consists of crystals of lanthanum oxychloride on a $TiO_2$ substrate, these crystals may be hydrated. It has been found that this product will effectively react with phosphate and bind it as an insoluble compound. It is believed that, if this final product is released in the human stomach and gastrointestinal tract, the product will bind the phosphate that is present and decrease the transfer of phosphate from the stomach and gastrointestinal tract to the blood stream. Therefore, the product of this invention may be used to limit the phosphorous content in the bloodstream of patients on kidney dialysis.

Figure 3:
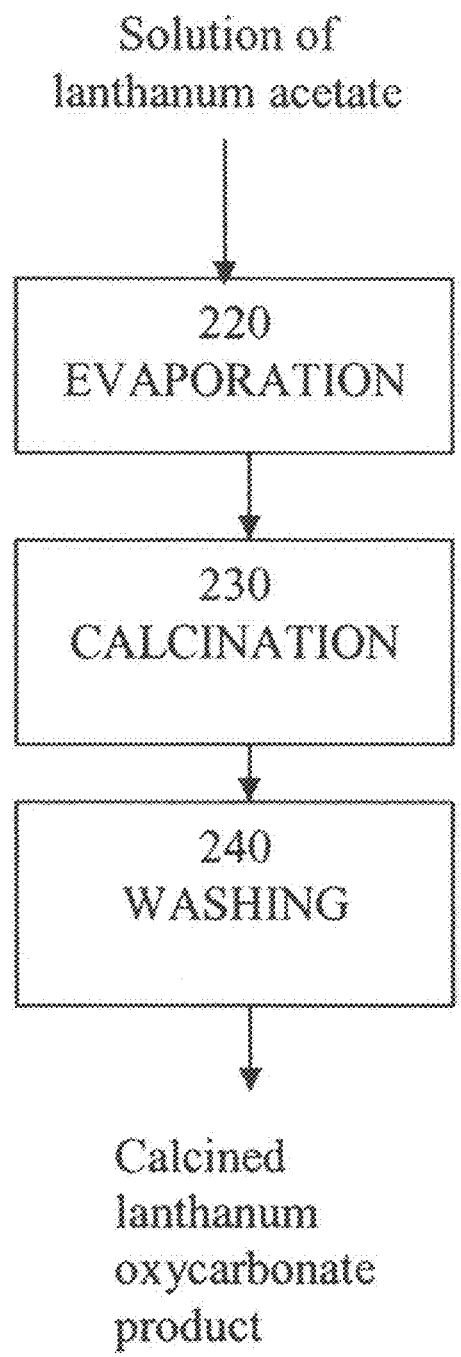
FIG. 3 is a flow sheet of a process according to the present invention that produces lanthanum oxycarbonate

According to another embodiment of the present invention, a process for making anhydrous lanthanum oxycarbonate is shown in FIG. 3. In this process, a solution of lanthanum acetate is made by any method. One method to make the lanthanum acetate solution is to dissolve commercial lanthanum acetate crystals in water or in an HCl solution.

The lanthanum acetate solution is evaporated to form an intermediate product. The evaporation 220 is conducted at a temperature higher than the boiling point of the lanthanum acetate solution but lower than the temperature where significant crystal growth occurs and under conditions to achieve substantially total evaporation. The resulting intermediate product may desirably be an amorphous solid formed as a thin film and may have a spherical shape or a shape as part of a sphere.

The intermediate product may then be calcined in any suitable calcination apparatus 230 by raising the temperature to a temperature between about 400° C. to about 800° C. for a period of time from about 2 to about 24 h and then cooled to room temperature. The cooled product may be washed 240 by immersing it in water or dilute acid, to remove any water-soluble phase that may still be present after the calcination step. The temperature and the length of time of the calcination process may be varied to adjust the particle size and the reactivity of the product.

The particles resulting from the calcination generally have a size between 1 and 1000 μm. The calcined particles consist of individual crystals, bound together in a structure with good physical strength and a porous structure. The individual crystals generally have a size between 20 nm and 10 μm.

The products made by methods shown in FIGS. 1, 2, and 3 comprise ceramic particles with a porous structure. Individual particles are in the micron size range. The particles are composed of crystallites in the nano-size range, fused together to create a structure with good strength and porosity.

The particles made according to the process of the present invention, have the following common properties:

a. They have low solubility in aqueous solutions, especially serum and gastro-intestinal fluid, compared to non-ceramic compounds.

b. Their hollow shape gives them a low bulk density compared to solid particles. Lower density particles are less likely to cause retention in the gastro-intestinal tract.

c. They have good phosphate binding kinetics. The observed kinetics are generally better than the commercial carbonate hydrates $La_2(CO_3)_3.H_2O$ and $La_2(CO_3)_3.4H_2O$. In the case of lanthanum oxychloride, the relationship between the amount of phosphate bound or absorbed and time tends to be closer to linear than for commercial hydrated lanthanum carbonates. The initial reaction rate is lower but does not significantly decrease with time over an extended period. This behavior is defined as linear or substantially linear binding kinetics. This is probably an indication of more selective phosphate binding in the presence of other anions.

d. Properties a, b, and c, above are expected to lead to less gastro-intestinal tract complications than existing products.

e. Because of their particular structure and low solubility, the products of the present invention have the potential to be used in a filtration device placed directly in the bloodstream.

Different lanthanum oxycarbonates have been prepared by different methods. It has been found that, depending on the method of preparation, lanthanum oxycarbonate compounds with widely different reaction rates are obtained.

Figure 4:
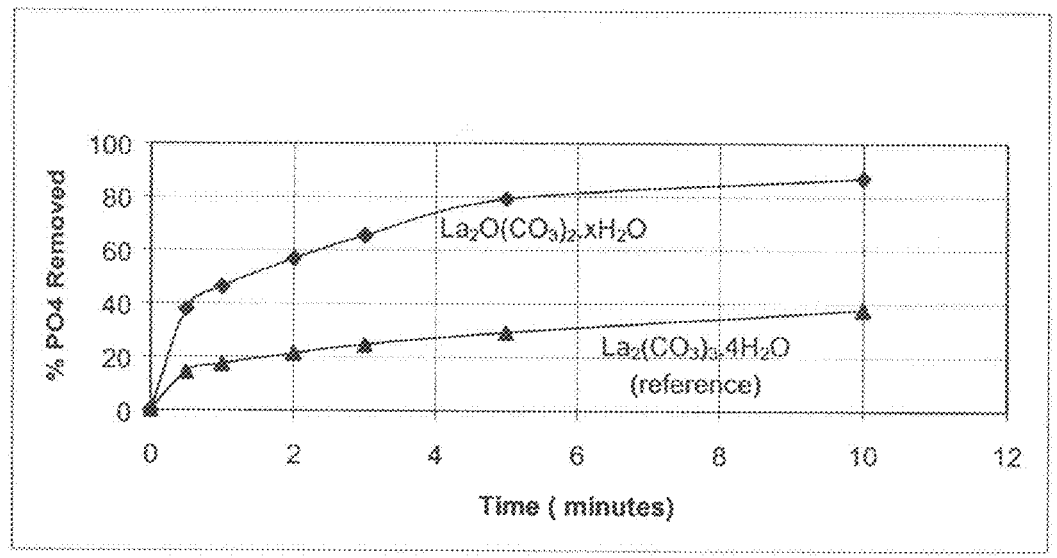
FIG. 4 is a graph showing the percentage of phosphate removed from a solution as a function of time by $LaO(CO_3)_2 \cdot x H_2O$, (where x is from and including 2 to and including 4), made according to the process of the present invention, as compared to the percentage of phosphate removed by commercial grade La carbonate $La_2(CO_3)_3 \cdot 4H_2O$ in the same conditions.

A desirable lanthanum oxycarbonate is $La_2O(CO_3)_2.xH_2O$, where $2 \leq x \leq 4$. This lanthanum oxycarbonate is preferred because it exhibits a relatively high rate of removal of phosphate. To determine the reactivity of the lanthanum oxycarbonate compound with respect to phosphate, the following procedure was used. A stock solution containing 13.75 g/l of anhydrous $Na_2HPO_4$ and 8.5 g/l of HCl is prepared. The stock solution is adjusted to pH 3 by the addition of concentrated HCl. 100 ml of the stock solution is placed in a beaker with a stirring bar. A sample of lanthanum oxycarbonate powder is added to the solution. The amount of lanthanum oxycarbonate powder is such that the amount of La in suspension is 3 times the stoichiometric amount needed to react completely with the phosphate. Samples of the suspension are taken at intervals, through a filter that separated all solids from the liquid. The liquid sample is analyzed for phosphorous. FIG. 4 shows that after 10 min, $La_2O(CO_3)_2.xH_2O$ has removed 86% of the phosphate in solution, whereas a commercial hydrated La carbonate $La_2(CO_3)_3.4H_2O$ removes only 38% of the phosphate in the same experimental conditions after the same time.

Figure 5:
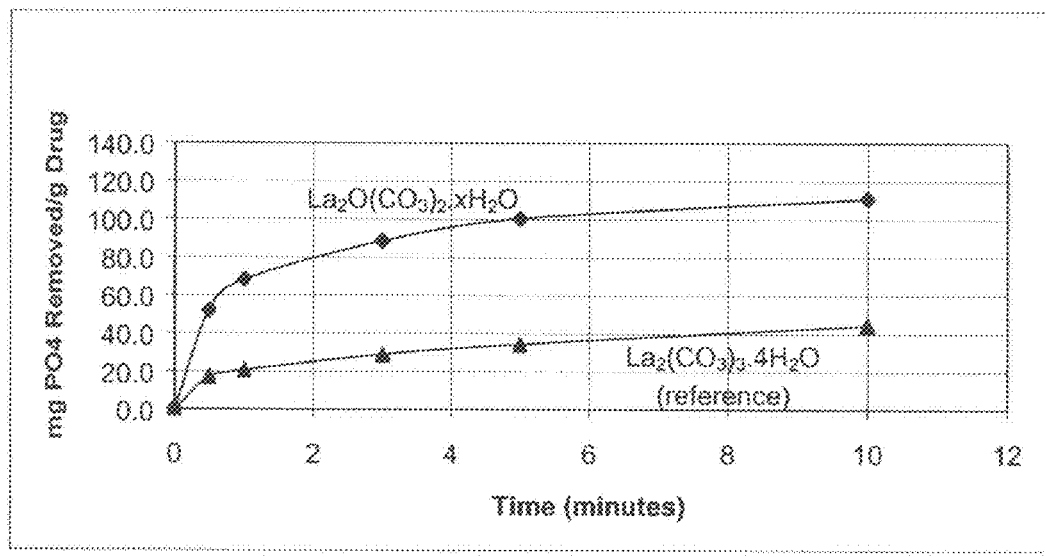
FIG. 5 is a graph showing the amount of phosphate removed from a solution as a function of time per g of a lanthanum compound used as a drug to treat hyperphosphatemia. The drug in one case is $La_2O(CO_3)_2 \cdot x H_2O$ (where x is from and including 2 to and including 4), made according to the process of the present invention. In the comparative case the drug is commercial grade La carbonate $La_2(CO_3)_3 \cdot 4H_2O$.

FIG. 5 shows that the $La_2O(CO_3)_2.xH_2O$ depicted in FIG. 4 has a capacity of phosphate removal of 110 mg $PO_4$ removed/g of La compound after 10 min in the conditions described above, compared to 45 mg $PO_4$/g for the commercial La carbonate taken as reference.

Figure 6:
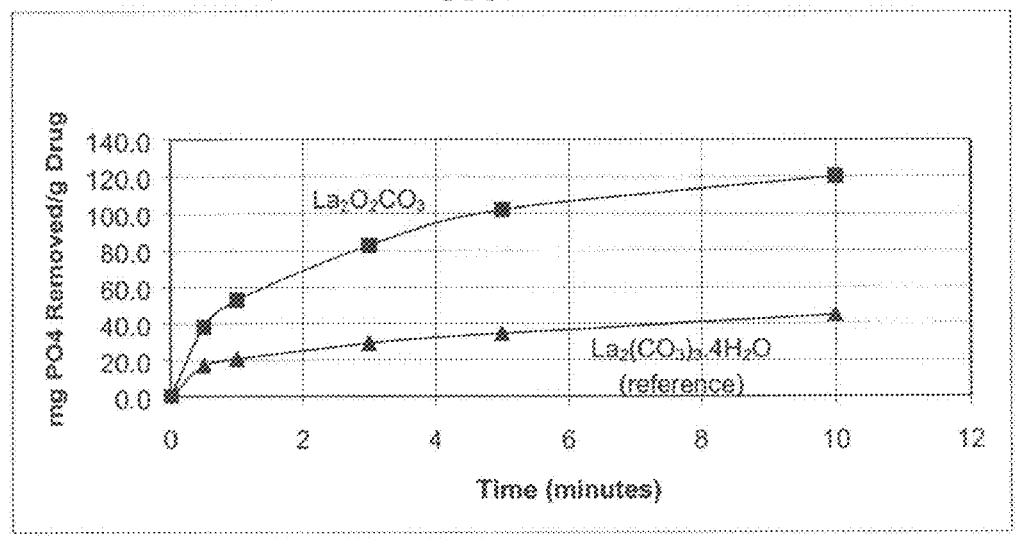
FIG. 6 is a graph showing the amount of phosphate removed from a solution as a function of time per g of a lanthanum compound used as a drug to treat hyperphosphatemia. The drug in one case is $La_2O_2CO_3$ made according to the process of the present invention. In the comparative case the drug is commercial grade La carbonate $La_2(CO_3)_3 \cdot 4H_2O$.

Another preferred lanthanum carbonate is the anhydrous La oxycarbonate $La_2O_2CO_3$. This compound is preferred because of its particularly high binding capacity for phosphate, expressed as mg $PO_4$ removed/g of compound. FIG. 6 shows that $La_2O_2CO_3$ binds 120 mg $PO_4$/g of La compound after 10 min, whereas $La_2(CO_3)_3.4H_2O$ used as reference only binds 45 mg $PO_4$/g La compound.

Figure 7:
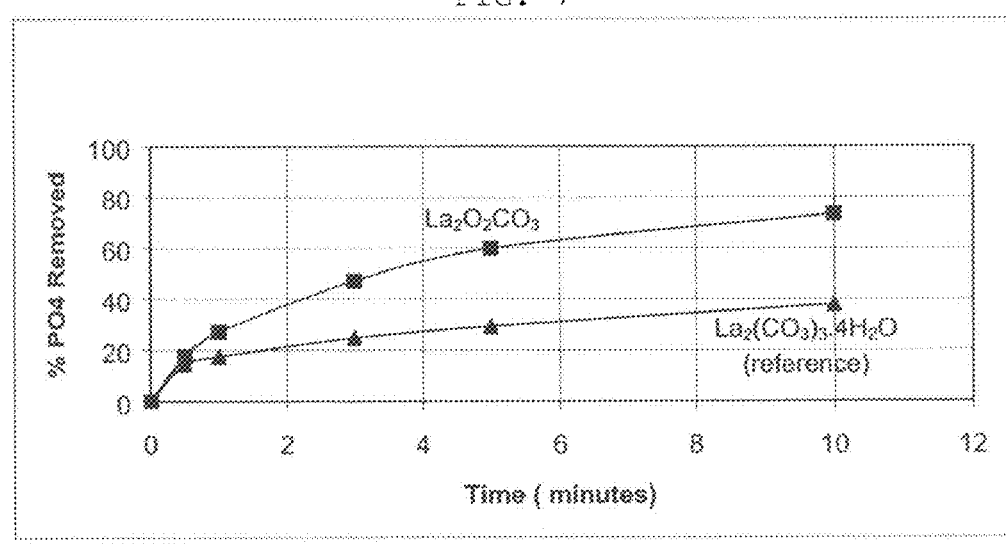
FIG. 7 is a graph showing the percentage of phosphate removed as a function of time by $La_2O_2CO_3$ made according to the process of the present invention, as compared to the percentage of phosphate removed by commercial grade La carbonate $La_2(CO_3)_3 \cdot 4H_2O$.

FIG. 7 shows the rate of reaction with phosphate of the oxycarbonate $La_2O_2CO_3$. After 10 min of reaction, 73% of the phosphate had been removed, compared to 38% for commercial lanthanum carbonate used as reference.

Samples of different oxycarbonates have been made by different methods as shown in Table 1 below.

TABLE 1

| Sample | Compound | Example number corresponding to manufacturing method | BET surface area $m^2/g$ | Fraction of $PO_4$ remaining after 10 min | Initial 1st order rate constant $k_1$ $(min^{-1})$ |
|---|---|---|---|---|---|
| 1 | $La_2O(CO_3)_2.xH_2O$ | 11 | 41.3 | 0.130 | 0.949 |
| 2 | $La_2O(CO_3)_2.xH_2O$ | 11 | 35.9 | 0.153 | 0.929 |
| 3 | $La_2O(CO_3)_2.xH_2O$ | 11 | 38.8 | 0.171 | 0.837 |
| 4 | $La_2CO_5$ (4 h milling) | 7 | 25.6 | 0.275 | 0.545 |
| 5 | $La_2O_2CO_3$ | 5 | 18 | 0.278 | 0.483 |
| 6 | $La_2CO_5$ (2 h milling) | 7 | 18.8 | 0.308 | 0.391 |
| 7 | $La_2O_2CO_3$ | 7 | 16.5 | 0.327 | 0.36 |
| 8 | $La_2CO_5$ (no milling) | 5 | 11.9 | 0.483 | 0.434 |
| 9 | $La_2(CO_3)_3.4H_2O$ | commercial sample | 4.3 | 0.623 | 0.196 |
| 10 | $La_2(CO_3)_3.1H_2O$ | commercial sample | 2.9 | 0.790 | 0.094 |

For each sample, the surface area measured by the BET method and the fraction of phosphate remaining after 10 min of reaction have been tabulated. The table also shows the rate constant $k_1$ corresponding to the initial rate of reaction of phosphate, assuming the reaction is first order in phosphate concentration. The rate constant $k_1$ is defined by the following equation:

$$d[PO_4]/dt = -k_1[PO_4]$$

where $[PO_4]$ is the phosphate concentration in solution (mol/liter), t is time (min) and $k_1$ is the first order rate constant $(min^{-1})$. The table gives the rate constant for the initial reaction rate, i.e. the rate constant calculated from the experimental points for the first minute of the reaction.

Figure 8:
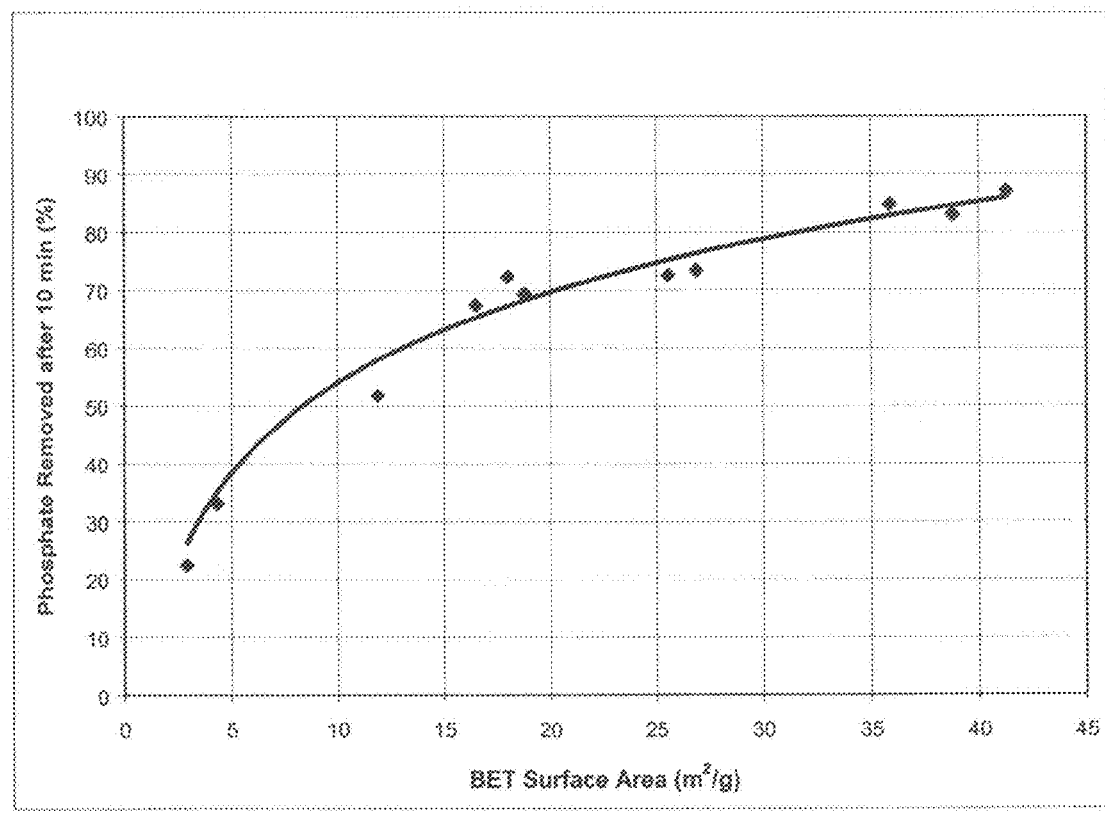
FIG. 8 is a graph showing a relationship between the specific surface area of the oxycarbonates made following the process of the present invention and the amount of phosphate bound or removed from solution 10 min after the addition of the oxycarbonate.

FIG. 8 shows that there is a good correlation between the specific surface area and the amount of phosphate reacted after 10 min. It appears that in this series of tests, the most important factor influencing the rate of reaction is the surface area, independently of the composition of the oxycarbonate or the method of manufacture. A high surface area can be achieved by adjusting the manufacturing method or by milling a manufactured product.

Figure 9:
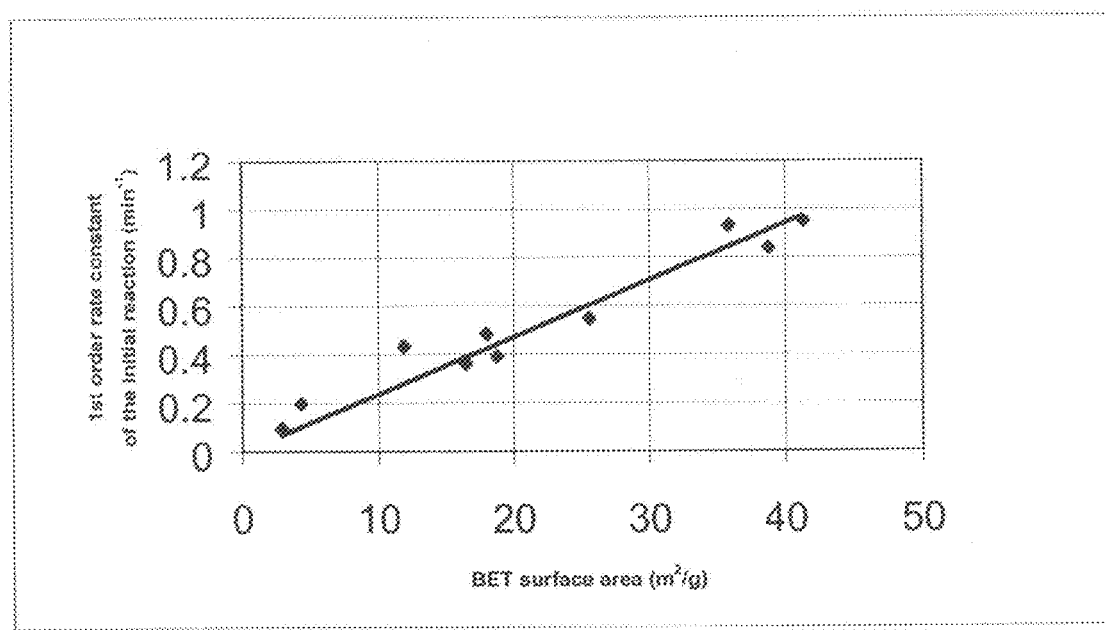
FIG. 9 is a graph showing a linear relationship between the specific surface area of the oxycarbonates of this invention and the first order rate constant calculated from the initial rate of reaction of phosphate.

FIG. 9 shows that a good correlation is obtained for the same compounds by plotting the first order rate constant as given in Table 1 and the BET specific surface area. The correlation can be represented by a straight line going through the origin. In other words, within experimental error, the initial rate of reaction appears to be proportional to the phosphate concentration and also to the available surface area.

Without being bound by any theory, it is proposed that the observed dependence on surface area and phosphate concentration may be explained by a nucleophilic attack of the phosphate ion on the La atom in the oxycarbonate, with resultant formation of lanthanum phosphate $LaPO_4$. For example, if the oxycarbonate is $La_2O_2CO_3$, the reaction will be:

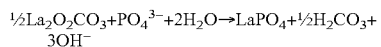
$3OH^-$

If the rate is limited by the diffusion of the $PO_4^{3-}$ ion to the surface of the oxycarbonate and the available area of oxycarbonate, the observed relationship expressed in FIG. 9 can be explained. This mechanism does not require La to be present as a dissolved species. The present reasoning also provides an explanation for the decrease of the reaction rate after the first minutes: the formation of lanthanum phosphate on the surface of the oxycarbonate decreases the area available for reaction.

In general, data obtained at increasing pH show a decrease of the reaction rate. This may be explained by the decrease in concentration of the hydronium ion ($H_3O^+$), which may catalyze the reaction by facilitating the formation of the carbonic acid molecule from the oxycarbonate.

Figure 10:
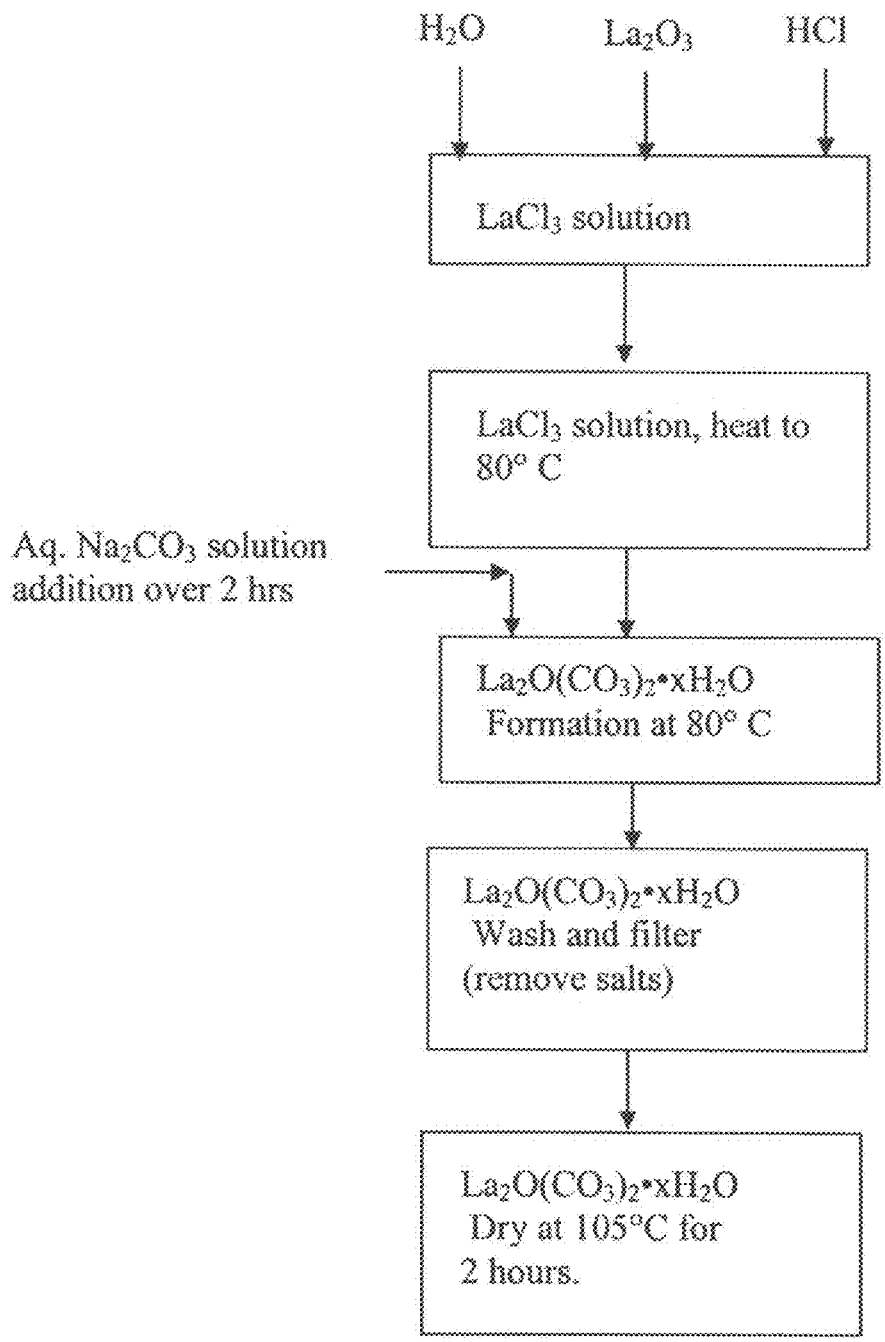
FIG. 10 is a flow sheet of a process according to the present invention that produces lanthanum oxycarbonate hydrate $La_2(CO_3)_2 \cdot xH_2O$

Turning now to FIG. 10, another process for making lanthanum oxycarbonate and in particular, lanthanum oxycarbonate tetra hydrate, is shown. First, an aqueous solution of lanthanum chloride is made by any method. One method to make the solution is to dissolve commercial lanthanum chloride crystals in water or in an HCl solution. Another method to make the lanthanum chloride solution is to dissolve lanthanum oxide in a hydrochloric acid solution.

The $LaCl_3$ solution is placed in a well-stirred tank reactor. The $LaCl_3$ solution is then heated to 80° C. A previously prepared analytical grade sodium carbonate is steadily added over a period of 2 hours with vigorous mixing. The mass of sodium carbonate required is calculated at 6 moles of sodium carbonate per 2 moles of $LaCl_3$. When the required mass of sodium carbonate solution is added, the resultant slurry or suspension is allowed to cure for 2 hours at 80° C. The suspension is then filtered and washed with demineralized water to produce a clear filtrate. The filter cake is placed in a convection oven at 105° C. for 2 hours or until a stable weight is observed. The initial pH of the $LaCl_3$ solution is 2, while the final pH of the suspension after cure is 5.5. A white powder is produced. The resultant powder is a lanthanum oxycarbonate four hydrate ($La_2O(CO_3)_2.xH_2O$). The number of water molecules in this compound is approximate and may vary between 2 and 4 (and including 2 and 4).

Figure 11:
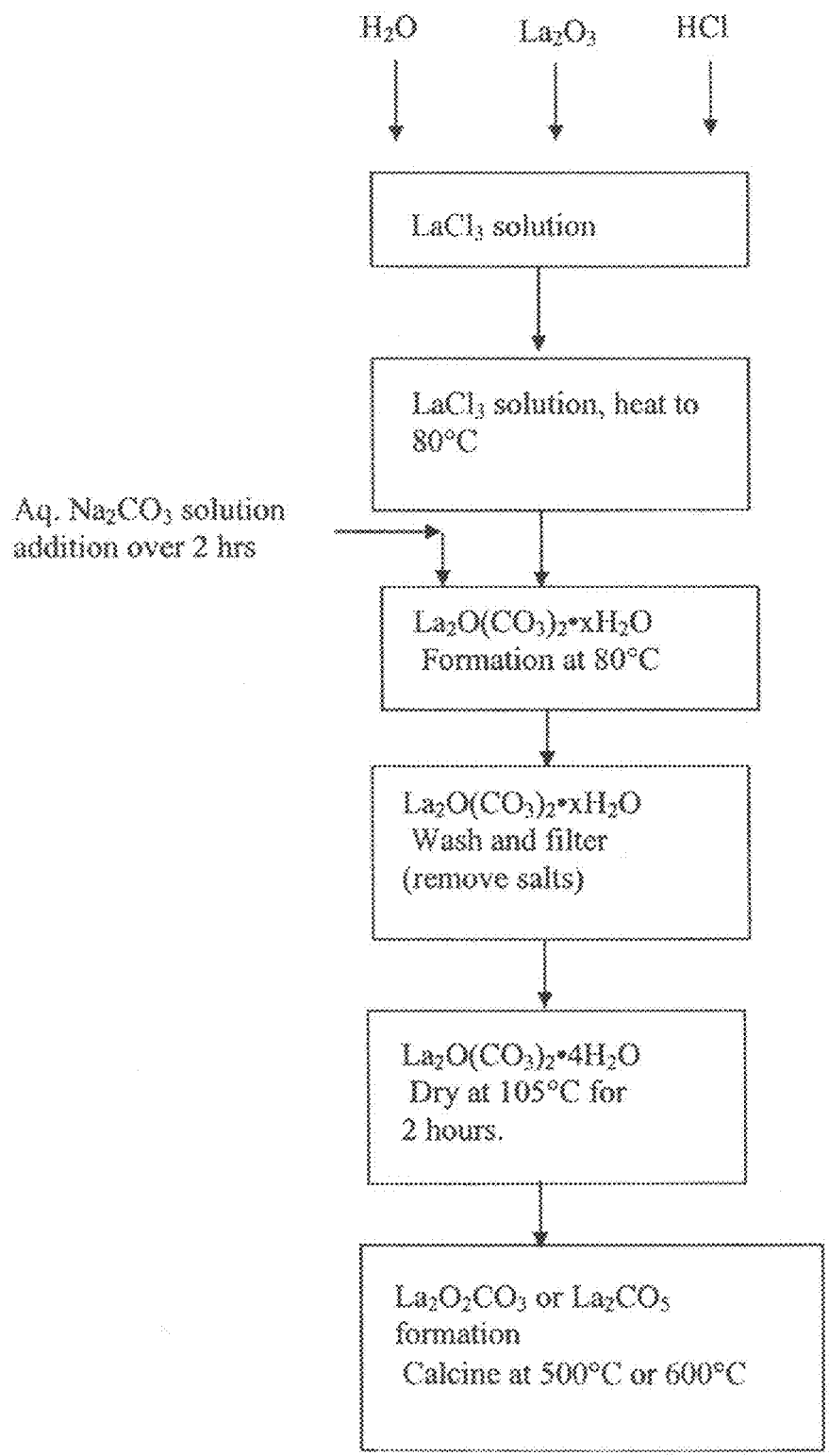
FIG. 11 is a flow sheet of a process according to the present invention that produces anhydrous lanthanum oxycarbonate $La_2O_2CO_3$ or $La_2CO_5$.

Turning now to FIG. 11 another process for making anhydrous lanthanum oxycarbonate is shown. First, an aqueous solution of lanthanum chloride is made by any method. One method to make the solution is to dissolve commercial lanthanum chloride crystals in water or in an HCl solution. Another method to make the lanthanum chloride solution is to dissolve lanthanum oxide in a hydrochloric acid solution.

The $LaCl_3$ solution is placed in a well-stirred tank reactor. The $LaCl_3$ solution is then heated to 80° C. A previously prepared analytical grade sodium carbonate is steadily added over 2 hours with vigorous mixing. The mass of sodium carbonate required is calculated at 6 moles of sodium carbonate per 2 moles of $LaCl_3$. When the required mass of sodium carbonate solution is added the resultant slurry or suspension is allowed to cure for 2 hours at 80° C. The suspension is then washed and filtered removing NaCl (a byproduct of the reaction) to produce a clear filtrate. The filter cake is placed in a convection oven at 105° C. for 2 hours or until a stable weight is observed. The initial pH of the $LaCl_3$ solution is 2.2, while the final pH of the suspension after cure is 5.5. A white lanthanum oxycarbonate hydrate powder is produced. Next the lanthanum oxycarbonate hydrate is placed in an alumina tray, which is placed in a high temperature muffle furnace. The white powder is heated to 500° C. and held at that temperature for 3 hours. Anhydrous $La_2C_2O_3$ is formed.

Alternatively, the anhydrous lanthanum oxycarbonate formed as indicated in the previous paragraph may be heated at 500° C. for 15 to 24 h instead of 3 h or at 600° C. instead of 500° C. The resulting product has the same chemical formula, but shows a different pattern in an X-Ray diffraction scan and exhibits a higher physical strength and a lower surface area. The product corresponding to a higher temperature or a longer calcination time is defined here as $La_2CO_5$.

Figure 31:
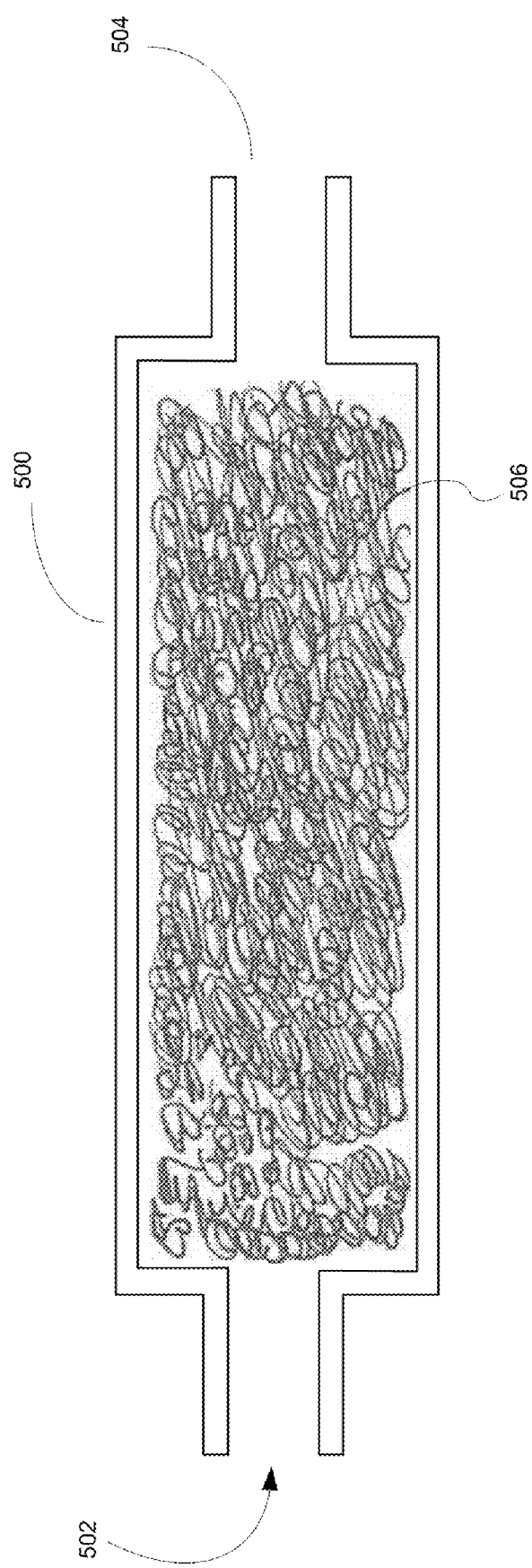
FIG. 31 shows a device having an inlet, an outlet, and one or more compounds of the present invention disposed between the inlet and the outlet.

Turning now to FIG. 31, a device 500 having an inlet 502 and an outlet 504 is shown. The device 500 may be in the form of a filter or other suitable container. Disposed between the inlet 502 and the outlet 504 is a substrate 506 in the form of a plurality of one or more compounds of the present invention. The device may be fluidically connected to a dialysis machine through which the blood flows, to directly remove phosphate by reaction of the rare-earth compound with phosphate in the bloodstream. In this connection, the present invention also contemplates a method of reducing the amount of phosphate in blood that comprises contacting the blood with one or more compounds of the present invention for a time sufficient to reduce the amount of phosphate in the blood.

In yet another aspect of the present invention, the device 500 may be provided in a fluid stream so that a fluid containing a metal, metal ion, phosphate or other ion may be passed from the inlet 502 through the substrate 506 to contact the compounds of the present invention and out the outlet 504. Accordingly, in one aspect of the present invention a method of reducing the content of a metal in a fluid, for example water, comprises flowing the fluid through a device 500 that contains one or more compounds of the present invention to reduce the amount of metal present in the water.

The following examples are meant to illustrate but not limit the present invention.

EXAMPLE 1

Figure 12:
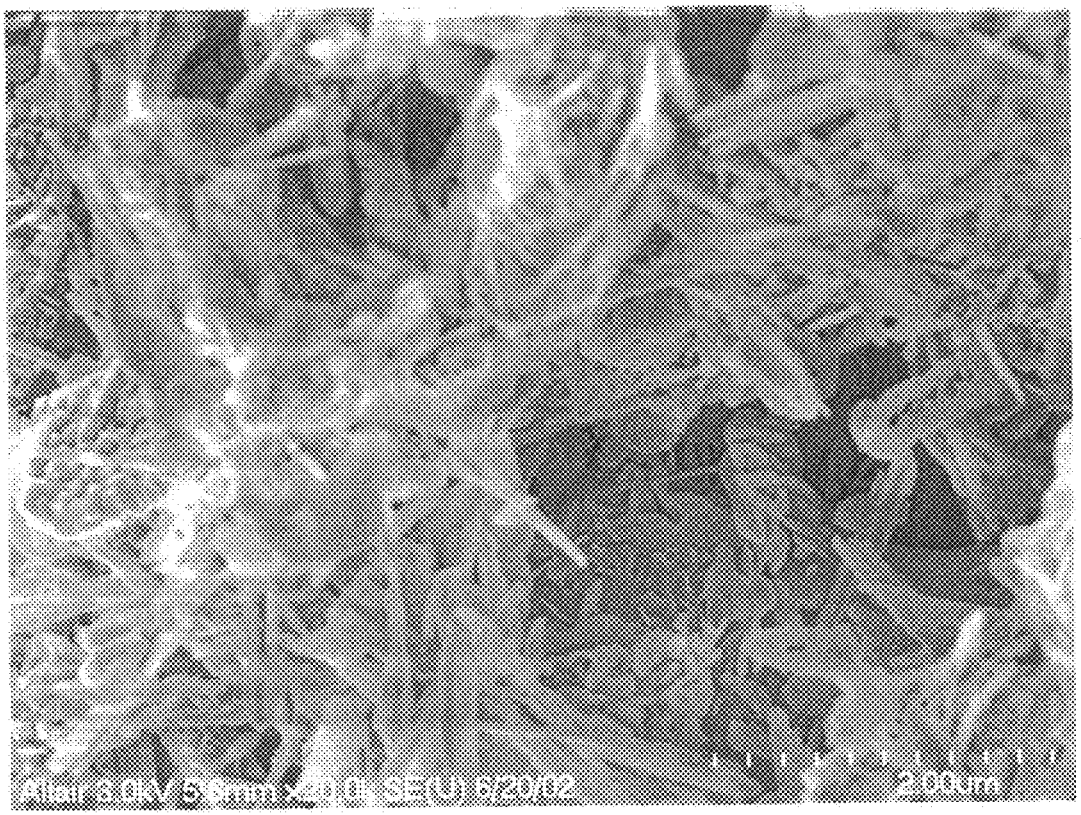
FIG. 12 is a scanning electron micrograph of lanthanum oxychloride, made following the process of the present invention.
Figure 13:
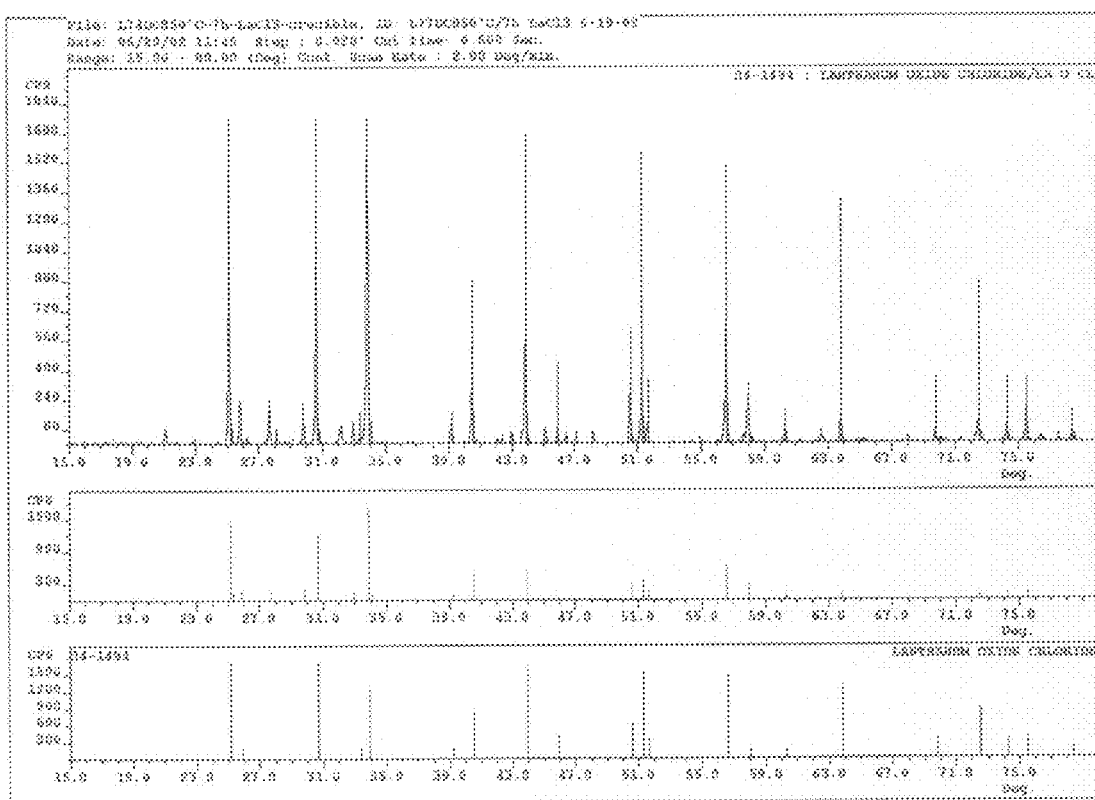
FIG. 13 is an X-Ray diffraction scan of lanthanum oxychloride LaOCl made according to the process of the present invention and compared with a standard library card of lanthanum oxychloride.

An aqueous solution containing 100 g/l of La as lanthanum chloride is injected in a spray dryer with an outlet temperature of 250° C. The intermediate product corresponding to the spray-drying step is recovered in a bag filter. This intermediate product is calcined at 900° C. for 4 hours. FIG. 12 shows a scanning electron micrograph of the product, enlarged 25,000 times. The micrograph shows a porous structure formed of needle-like particles. The X-Ray diffraction pattern of the product (FIG. 13) shows that it consists of lanthanum oxychloride LaOCl.

Figure 14:
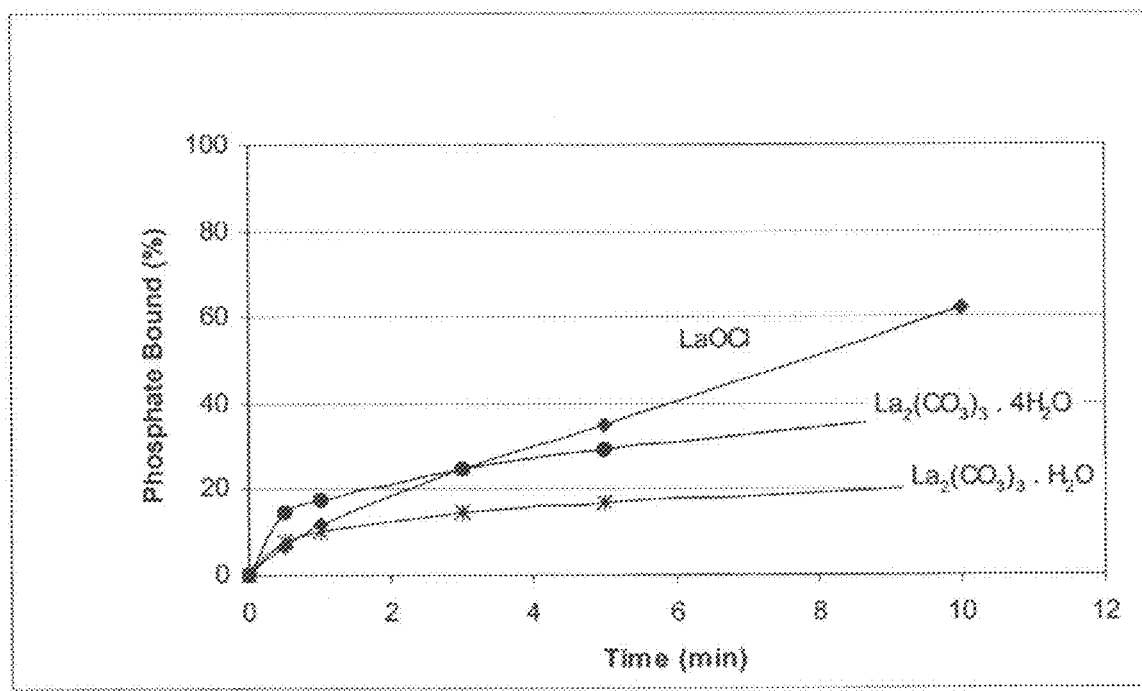
FIG. 14 is a graph showing the percentage of phosphate removed from a solution as a function of time by LaOCl made according to the process of the present invention, as compared to the amount of phosphate removed by commercial grades of La carbonate $La_2(CO_3)_3 \cdot H_2O$ and $La_2(CO_3)_3 \cdot 4H_2O$ in the same conditions.

To determine the reactivity of the lanthanum compound with respect to phosphate, the following test was conducted. A stock solution containing 13.75 g/l of anhydrous $Na_2HPO_4$ and 8.5 g/l of HCl was prepared. The stock solution was adjusted to pH 3 by the addition of concentrated HCl. An amount of 100 ml of the stock solution was placed in a beaker with a stirring bar. The lanthanum oxychloride from above was added to the solution to form a suspension. The amount of lanthanum oxychloride was such that the amount of La in suspension was 3 times the stoichiometric amount needed to react completely with the phosphate. Samples of the suspension were taken at time intervals, through a filter that separated all solids from the liquid. The liquid sample was analyzed for phosphorous. FIG. 14 shows the rate of phosphate removed from solution.

EXAMPLE 2 (COMPARATIVE EXAMPLE)

To determine the reactivity of a commercial lanthanum with respect to phosphate, the relevant portion of Example 1 was repeated under the same conditions, except that commercial lanthanum carbonate $La_2(CO_3)_3.H_2O$ and $La_2(CO_3)_3.4H_2O$ was used instead of the lanthanum oxychloride of the present invention. Additional curves on FIG. 14 show the rate of removal of phosphate corresponding to commercial lanthanum carbonate $La_2(CO_3)_3.H2O$ and $La_2(CO_3).4H_2O$. FIG. 14 shows that the rate of removal of phosphate with the commercial lanthanum carbonate is faster at the beginning but slower after about 3 minutes.

EXAMPLE 3

Figure 15:
FIG. 15 shows a scanning electron micrograph of $La_2O(CO_3)_2 \cdot x\, H_2O$, where x is from and including 2 to and including 4.
Figure 16:
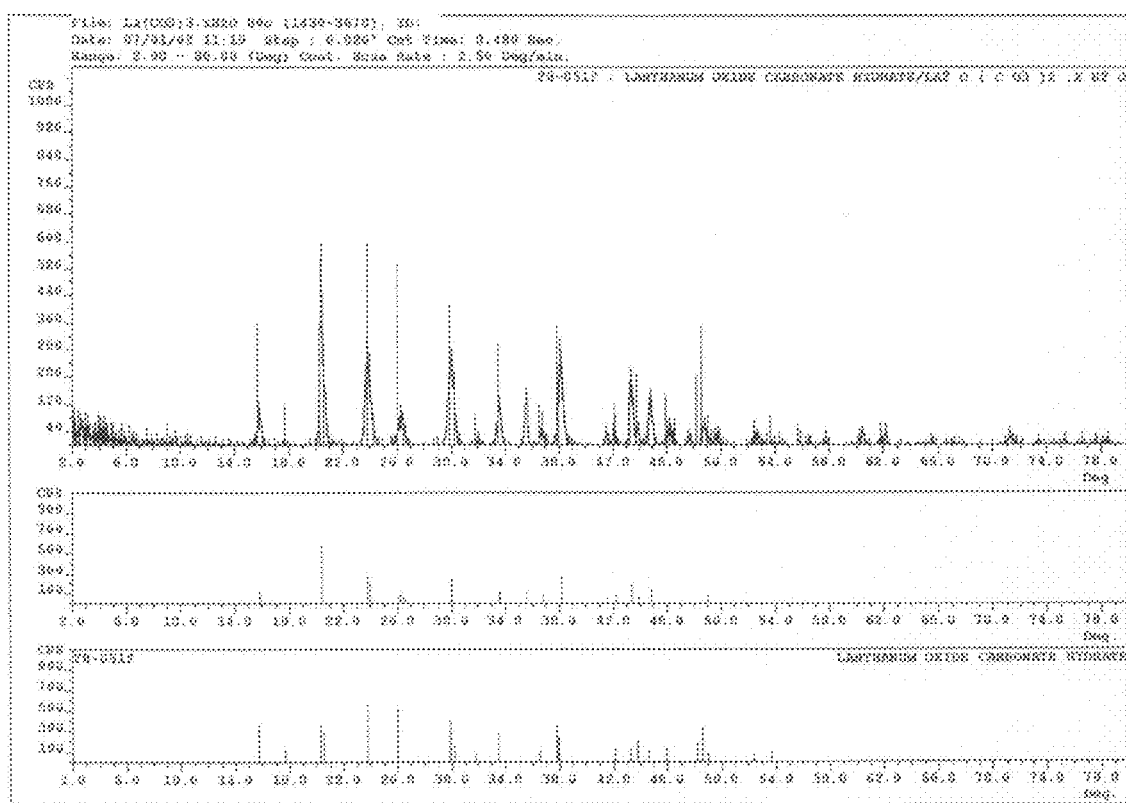
FIG. 16 is an X-Ray diffraction scan of $La_2O(CO_3)_2 \cdot x\, H_2O$ produced according to the present invention and includes a comparison with a "library standard" of $La_2O(CO_3)_2 \cdot xH_2O$ where x is from and including 2 to and including 4.

An aqueous HCl solution having a volume of 334.75 ml and containing $LaCl_3$ (lanthanum chloride) at a concentration of 29.2 wt % as $La_2O_3$ was added to a four liter beaker and heated to 80° C. with stirring. The initial pH of the $LaCl_3$ solution was 2.2. Two hundred and sixty five ml of an aqueous solution containing 63.59 g of sodium carbonate ($Na_2CO_3$) was metered into the heated beaker using a small pump at a steady flow rate for 2 hours. Using a Buchner filtering apparatus fitted with filter paper, the filtrate was separated from the white powder product. The filter cake was mixed four times with 2 liters of distilled water and filtered to wash away the NaCl formed during the reaction. The washed filter cake was placed into a convection oven set at 105° C. for 2 hours, or until a stable weight was observed. FIG. 15 shows a scanning electron micrograph of the product, enlarged 120,000 times. The micrograph shows the needle-like structure of the compound. The X-Ray diffraction pattern of the product (FIG. 16) shows that it consists of hydrated lanthanum oxycarbonate hydrate ($La_2O(CO_3)_2.xH_2O$), with $2 \leq x \leq 4$.

Figure 17:
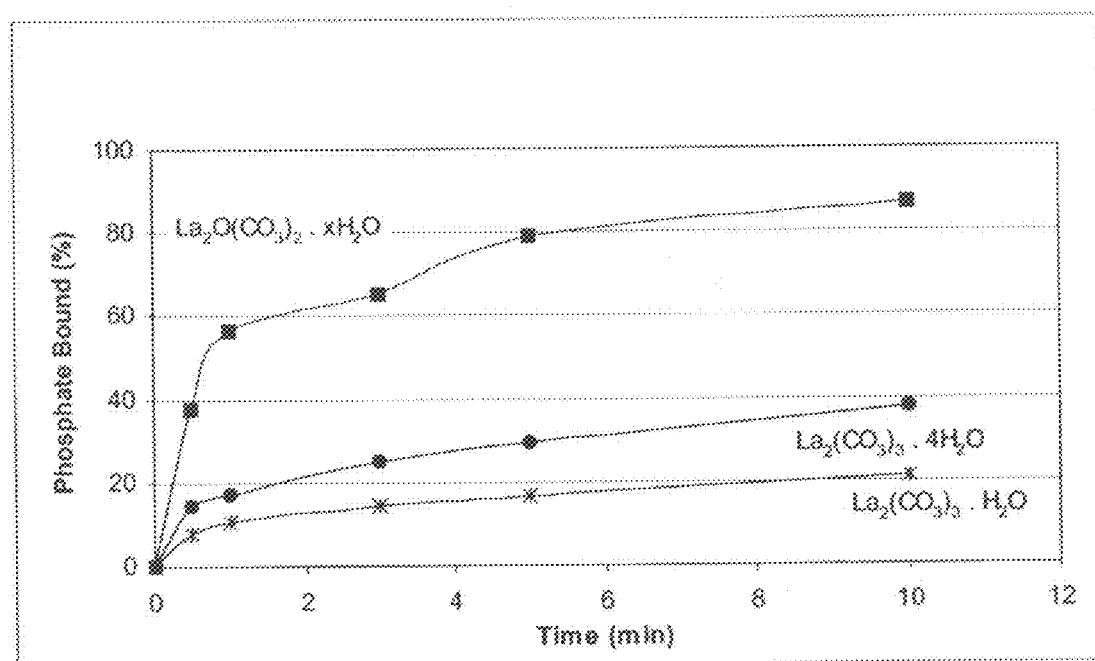
FIG. 17 is a graph showing the rate of removal of phosphorous from a solution by $La_2O(CO_3)2 \cdot xH_2O$ compared to the rate obtained with commercially available $La_2(CO_3)_3 \cdot H_2O$ and $La_2(CO_3)_3 \cdot 4H_2O$ in the same conditions.

To determine the reactivity of the lanthanum compound with respect to phosphate, the following test was conducted. A stock solution containing 13.75 g/l of anhydrous $Na_2HPO_4$ and 8.5 g/l of HCl was prepared. The stock solution was adjusted to pH 3 by the addition of concentrated HCl. An amount of 100 ml of the stock solution was placed in a beaker with a stirring bar. Lanthanum oxycarbonate hydrate powder made as described above was added to the solution. The amount of lanthanum oxycarbonate hydrate powder was such that the amount of La in suspension was 3 times the stoichiometric amount needed to react completely with the phosphate. Samples of the suspension were taken at time intervals through a filter that separated all solids from the liquid. The liquid sample was analyzed for phosphorous. FIG. 17 shows the rate of phosphate removed from solution.

EXAMPLE 4 (COMPARATIVE EXAMPLE)

To determine the reactivity of a commercial lanthanum with respect to phosphate, the second part of Example 3 was repeated under the same conditions, except that commercial lanthanum carbonate $La_2(CO_3)_3.H_2O$ and $La_2(CO_3)_3.4H_2O$ was used instead of the lanthanum oxychloride of the present invention. FIG. 17 shows the rate of phosphate removed using the commercial lanthanum carbonate $La_2(CO_3)3.H_2O$ and $La_2(CO_3)_3.4H_2O$. FIG. 17 shows that the rate of removal of phosphate with the lanthanum oxycarbonate is faster than with the commercial lanthanum carbonate hydrate ($La_2(CO_3)_3.H_2O$ and $La_2(CO_3)_3.4H_2O$).

EXAMPLE 5

An aqueous HCl solution having a volume of 334.75 ml and containing $LaCl_3$ (lanthanum chloride) at a concentration of 29.2 wt % as $La_2O_3$ was added to a 4 liter beaker and heated to 80° C. with stirring. The initial pH of the $LaCl_3$ solution was 2.2. Two hundred and sixty five ml of an aqueous solution containing 63.59 g of sodium carbonate ($Na_2CO_3$) was metered into the heated beaker using a small pump at a steady flow rate for 2 hours. Using a Buchner filtering apparatus fitted with filter paper the filtrate was separated from the white powder product. The filter cake was mixed four times with 2 liters of distilled water and filtered to wash away the NaCl formed during the reaction. The washed filter cake was placed into a convection oven set at 105° C. for 2 hours until a stable weight was observed. Finally, the lanthanum oxycarbonate was placed in an alumina tray in a muffle furnace. The furnace temperature was ramped to 500° C. and held at that temperature for 3 hours. The resultant product was determined to be anhydrous lanthanum oxycarbonate $La_2O_2CO_3$.

Figure 18:
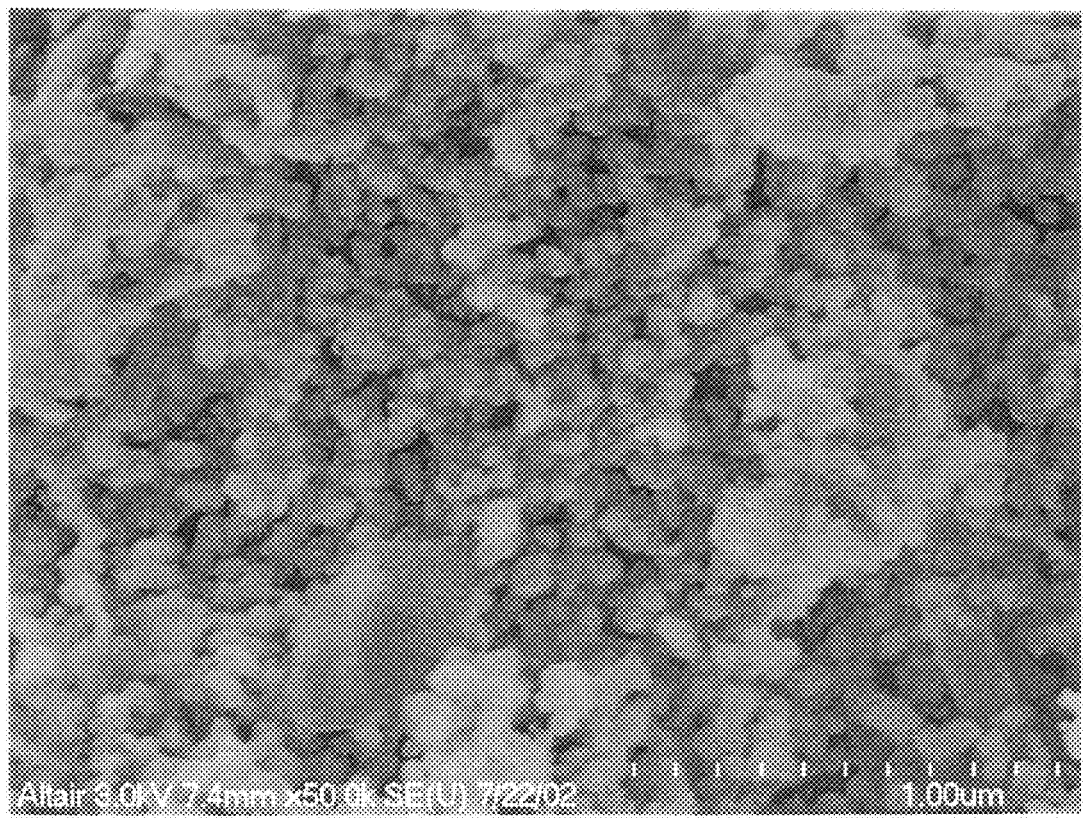
FIG. 18 is a scanning electron micrograph of anhydrous lanthanum oxycarbonate $La_2O_2CO_3$.
Figure 19:
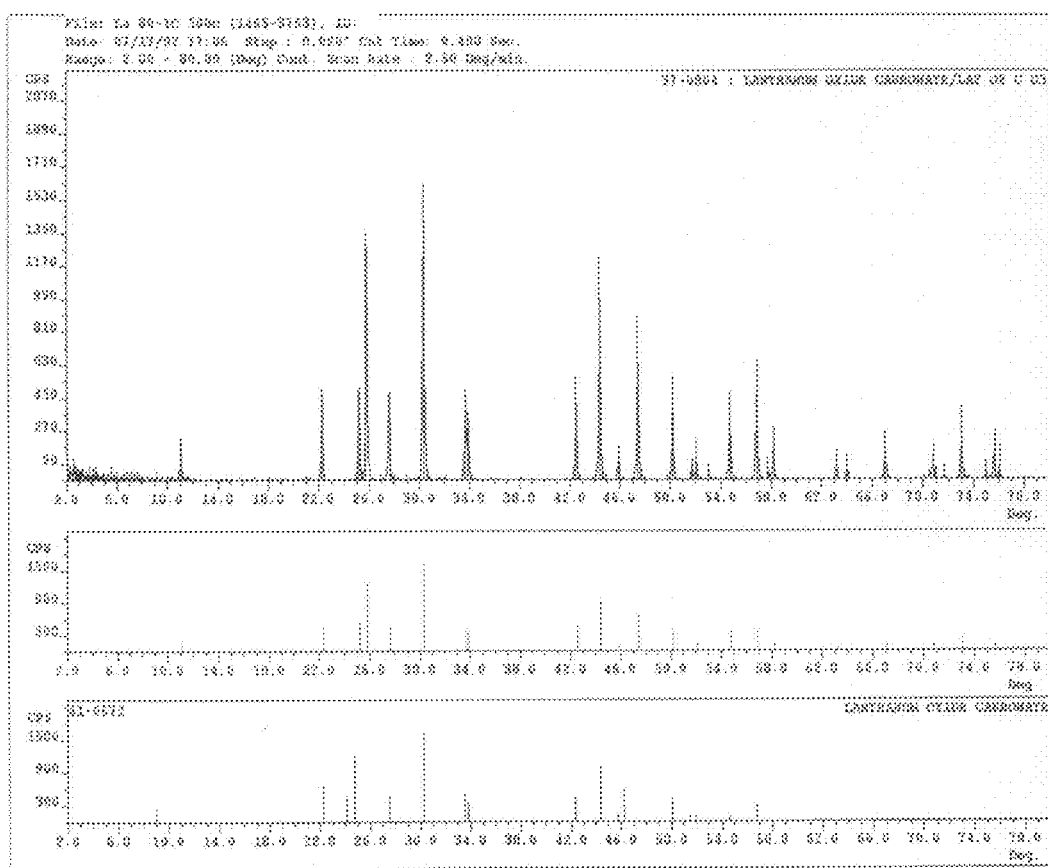
FIG. 19 is an X-Ray diffraction scan of anhydrous $La_2O_2CO_3$ produced according to the present invention and includes a comparison with a "library standard" of $La_2O_2CO_3$.

The process was repeated three times. In one case, the surface area of the white powder was determined to be 26.95 $m^2/gm$. In the other two instances, the surface area and reaction rate is shown in Table 1. FIG. 18 is a scanning electron micrograph of the structure, enlarged 60,000 times. The micrograph shows that the structure in this compound is made of equidimensional or approximately round particles of about 100 nm in size. FIG. 19 is an X-ray diffraction pattern showing that the product made here is an anhydrous lanthanum oxycarbonate written as $La_2O_2CO_3$.

Figure 20:
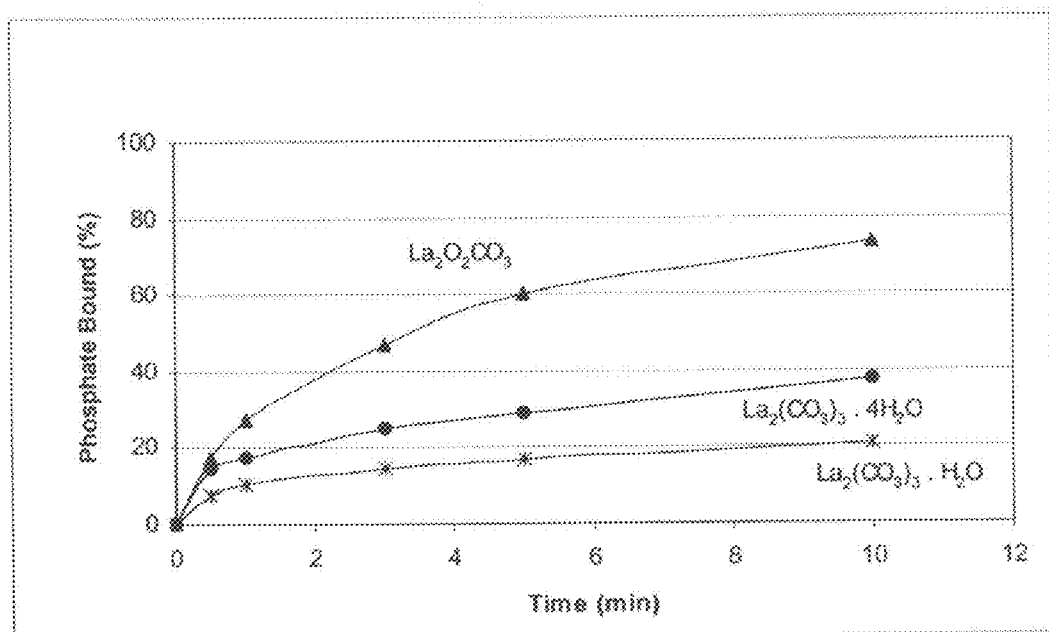
FIG. 20 is a graph showing the rate of phosphorous removal obtained with $La_2O_2CO_3$ made following the process of the present invention and compared to the rate obtained for commercially available $La_2(CO_3)_3 \cdot H_2O$ and $La_2(CO_3)_3 \cdot 4H_2O$.

To determine the reactivity of this lanthanum compound with respect to phosphate, the following test was conducted. A stock solution containing 13.75 g/l of anhydrous $Na_2HPO_4$ and 8.5 g/l of HCl was prepared. The stock solution was adjusted to pH 3 by the addition of concentrated HCl. An amount of 100 ml of the stock solution was placed in a beaker with a stirring bar. Anhydrous lanthanum oxycarbonate made as described above, was added to the solution. The amount of anhydrous lanthanum oxycarbonate was such that the amount of La in suspension was 3 times the stoichiometric amount needed to react completely with the phosphate. Samples of the suspension were taken at intervals, through a filter that separated all solids from the liquid. The liquid sample was analyzed for phosphorous. FIG. 20 shows the rate of phosphate removed.

EXAMPLE 6 (COMPARATIVE EXAMPLE)

To determine the reactivity of a commercial lanthanum with respect to phosphate, the second part of Example 5 was repeated under the same conditions, except that commercial lanthanum carbonate $La_2(CO_3)_3.H_2O$ and $La_2(CO_3)_3.4H_2O$ was used instead of the $La_2O_2CO_3$ of the present invention. FIG. 20 shows the rate of removal of phosphate using the commercial lanthanum carbonate $La_2(CO_3)_3.H_2O$ and $La_2(CO_3)_3.4H_2O$. FIG. 20 shows that the rate of removal of phosphate with the anhydrous lanthanum oxycarbonate produced according to the process of the present invention is faster than the rate observed with commercial lanthanum carbonate hydrate $La_2(CO_3)_3.H_2O$ and $La_2(CO_3)_34H_2O$.

EXAMPLE 7

Figure 21:
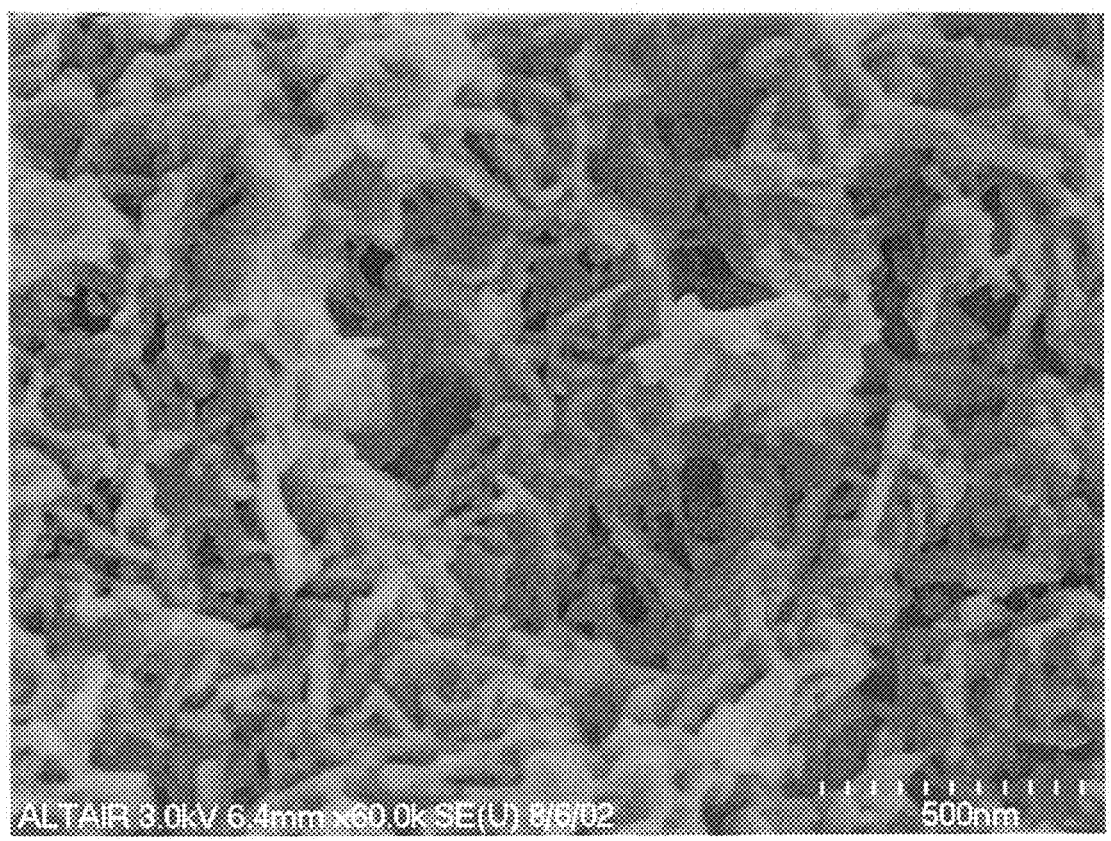
FIG. 21 is a scanning electron micrograph of $La_2CO_5$ made according to the process of the present invention.
Figure 22:
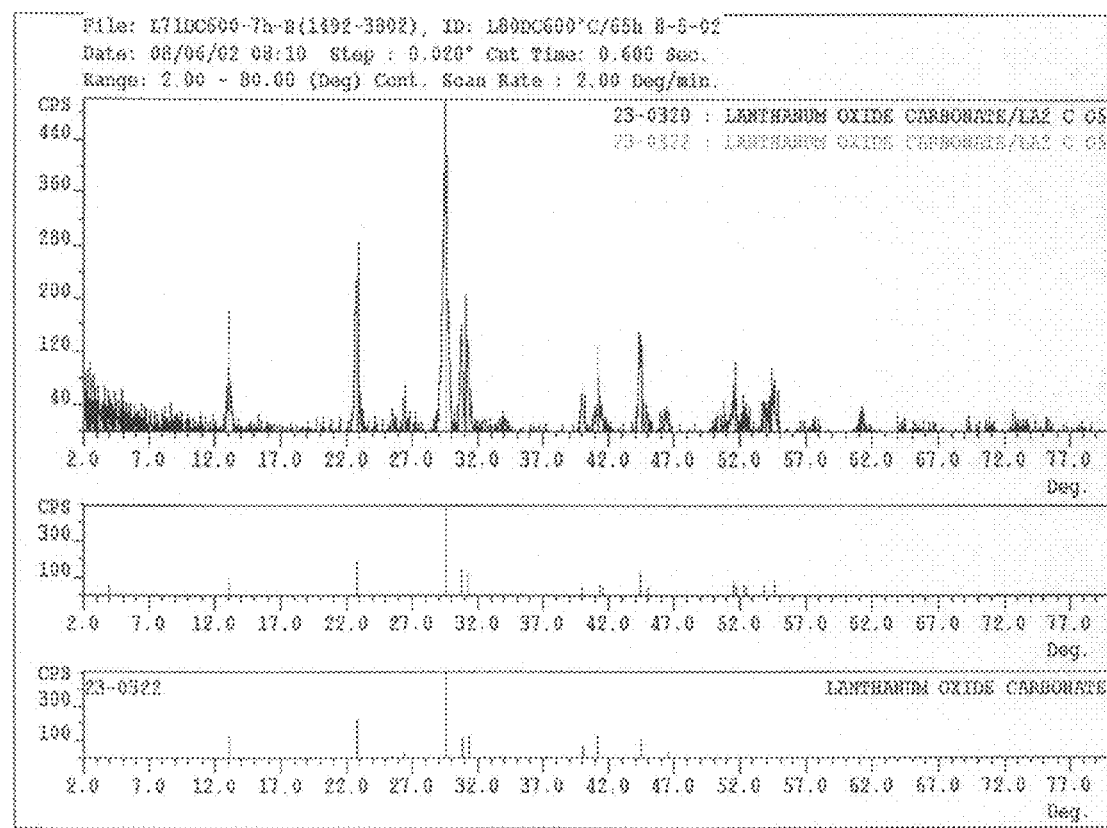
FIG. 22 is an X-Ray diffraction scan of anhydrous $La_2CO_5$ produced according to the present invention and includes a comparison with a "library standard" of $La_2CO_5$.

A solution containing 100 g/l of La as lanthanum acetate is injected in a spray-drier with an outlet temperature of 250° C. The intermediate product corresponding to the spray-drying step is recovered in a bag filter. This intermediate product is calcined at 600° C. for 4 hours. FIG. 21 shows a scanning electron micrograph of the product, enlarged 80,000 times. FIG. 22 shows the X-Ray diffraction pattern of the product and it shows that it consists of anhydrous lanthanum oxycarbonate. The X-Ray pattern is different from the pattern corresponding to Example 5, even though the chemical composition of the compound is the same. The formula for this compound is written as ($La_2CO_5$). Comparing FIGS. 21 and 18 shows that the compound of the present example shows a structure of leaves and needles as opposed to the round particles formed in Example 5. The particles may be used in a device to directly remove phosphate from an aqueous or non-aqueous medium, e.g., the gut or the bloodstream.

Figure 23:
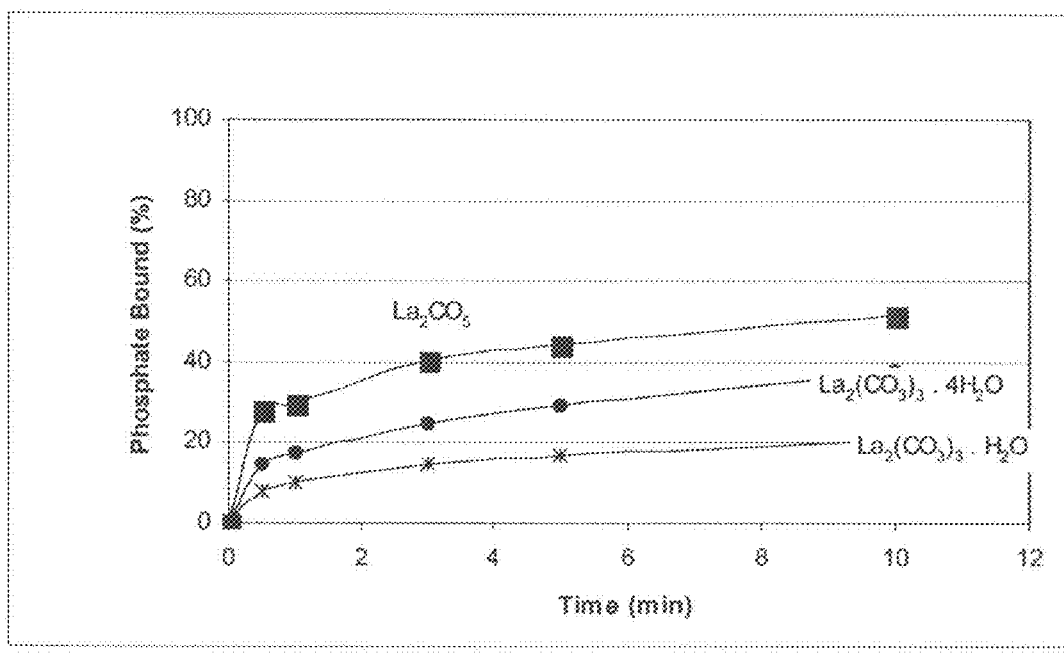
FIG. 23 is a graph showing the rate of phosphorous removal obtained with $La_2CO_5$ made following the process of the present invention and compared to the rate obtained for commercially available $La_2(CO_3)_3 \cdot H_2O$ and $La_2(CO_3)_3 \cdot 4H_2O$.

To determine the reactivity of the lanthanum compound with respect to phosphate, the following test was conducted. A stock solution containing 13.75 g/l of anhydrous $Na_2HPO_4$ and 8.5 g/l of HCl was prepared. The stock solution was adjusted to pH 3 by the addition of concentrated HCl. An amount of 100 ml of the stock solution was placed in a beaker with a stirring bar. $La_2CO_5$ powder, made as described above, was added to the solution. The amount of lanthanum oxycarbonate was such that the amount of La in suspension was 3 times the stoichiometric amount needed to react completely with the phosphate. Samples of the suspension were taken at intervals through a filter that separated all solids from the liquid. The liquid sample was analyzed for phosphorous. FIG. 23 shows the rate of phosphate removed from solution.

EXAMPLE 8 (COMPARATIVE EXAMPLE)

To determine the reactivity of a commercial lanthanum with respect to phosphate commercial lanthanum carbonate $La_2(CO_3)_3.H_2O$ and $La_2(CO_3)_3.4H_2O$ was used instead of the lanthanum oxycarbonate made according to the present invention as described above. FIG. 23 shows the rate of phosphate removal for the commercial lanthanum carbonate $La_2(CO_3)_3.H_2O$ and $La_2(CO_3)_3.4H_2O$. FIG. 23 also shows that the rate of phosphate removal with the lanthanum oxycarbonate is faster than the rate of phosphate removal with commercial lanthanum carbonate hydrate $La_2(CO_3)_3.H_2O$ and $La_2(CO_3)_3.4H_2O$.

EXAMPLE 9

Figure 24:
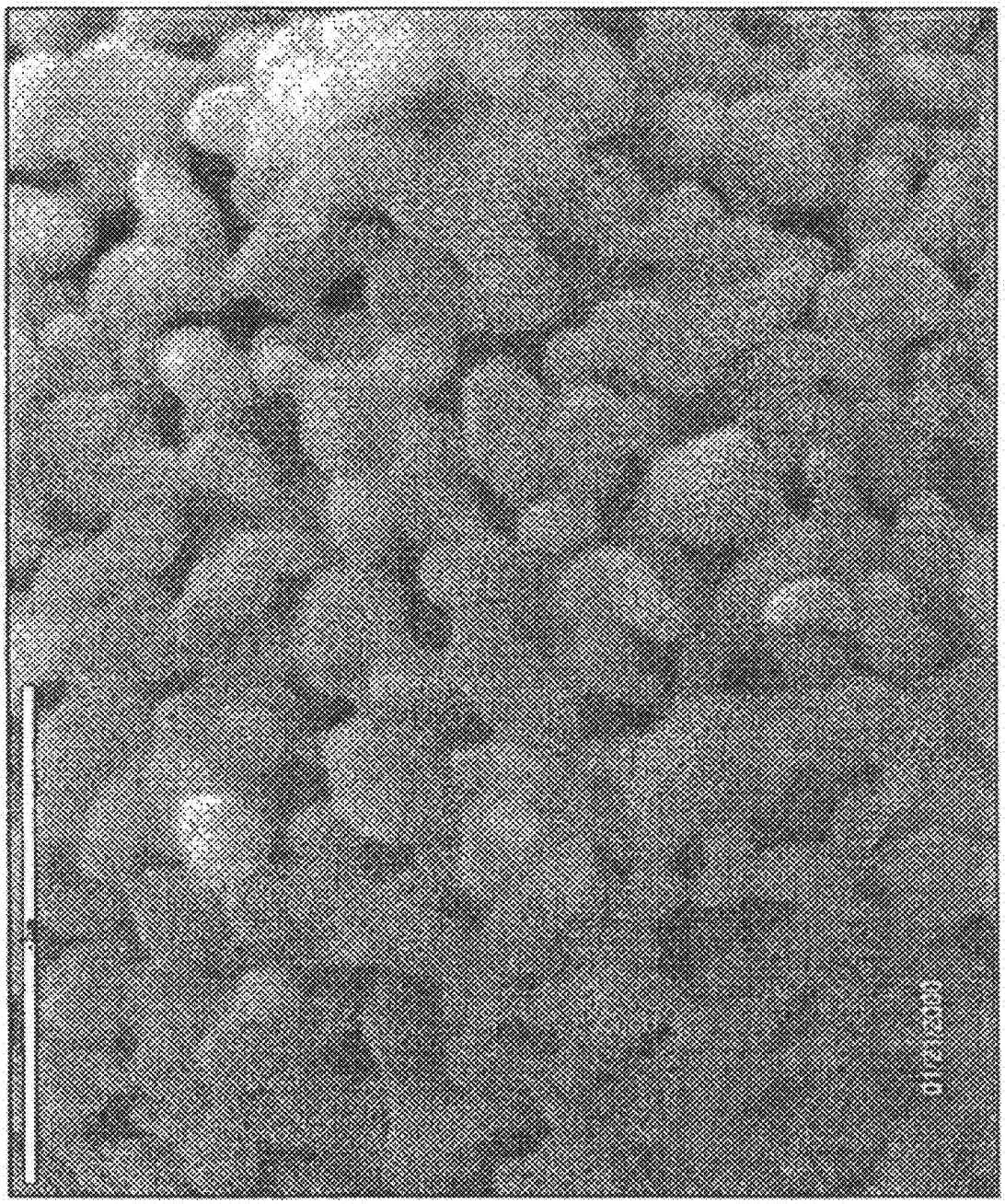
FIG. 24 is a scanning electron micrograph of $TiO_2$ support material made according to the process of the present invention.

To a solution of titanium chloride or oxychloride containing 120 g/l Ti and 450 g/l Cl is added the equivalent of 2.2 g/l of sodium phosphate $Na_3PO_4$. The solution is injected in a spray dryer with an outlet temperature of 250° C. The spray dryer product is calcined at 1050° C. for 4 h. The product is subjected to two washing steps in 2 molar HCl and to two washing steps in water. FIG. 24 is a scanning electron micrograph of the $TiO_2$ material obtained. It shows a porous structure with individual particles of about 250 nm connected in a structure. This structure shows good mechanical strength. This material can be used as an inert filtering material in a fluid stream such as blood.

EXAMPLE 10

Figure 25:
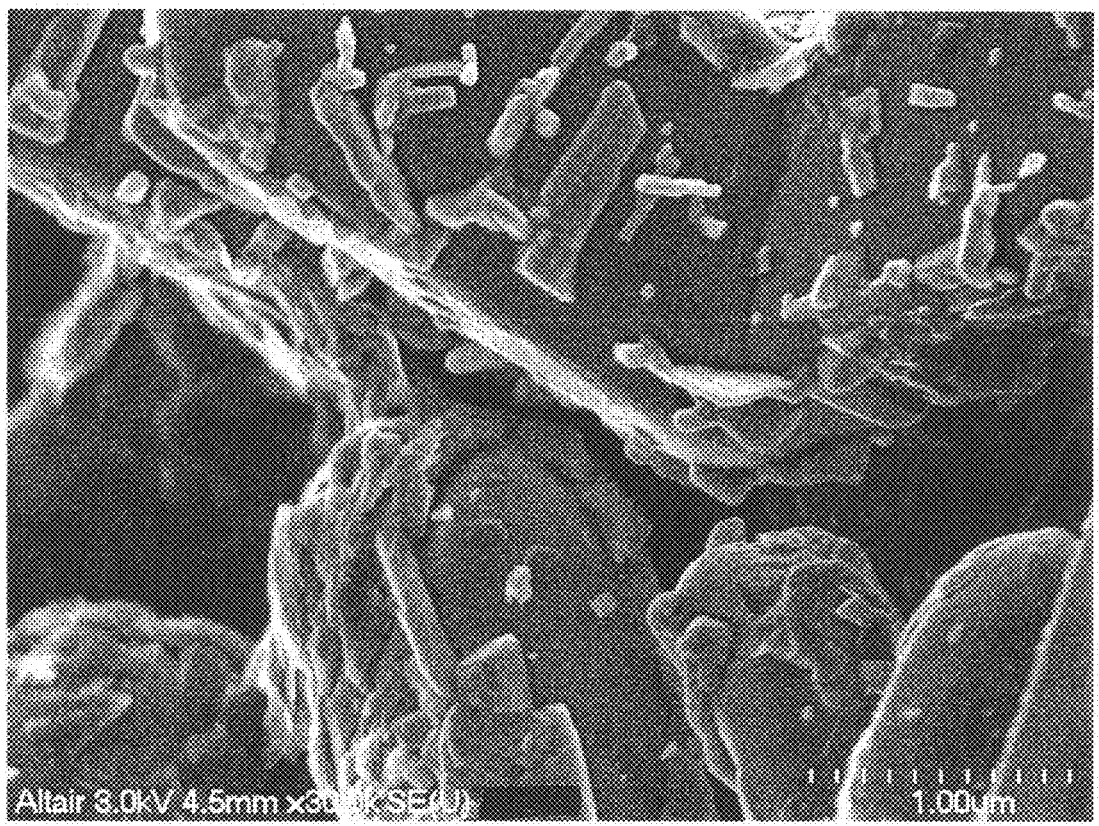
FIG. 25 is a scanning electron micrograph of a $TiO_2$ structure coated with LaOCl, made according to the process of the present invention, calcined at 800° C.

The product of Example 9 is re-slurried into a solution of lanthanum chloride containing 100 g/l La. The slurry contains approximately 30% $TiO_2$ by weight. The slurry is spray dried in a spray dryer with an outlet temperature of 250° C. The product of the spray drier is further calcined at 800° C. for 5 h. It consists of a porous $TiO_2$ structure with a coating of nano-sized lanthanum oxychloride. FIG. 25 is a scanning electron micrograph of this coated product. The electron micrograph shows that the $TiO_2$ particles are several microns in size. The LaOCl is present as a crystallized deposit with elongated crystals, often about 1 µm long and 0.1 µm across, firmly attached to the $TiO_2$ catalyst support surface as a film of nano-size thickness. The LaOCl growth is controlled by the $TiO_2$ catalyst support structure. Orientation of rutile crystals works as a template for LaOCl crystal growth. The particle size of the deposit can be varied from the nanometer to the micron range by varying the temperature of the second calcination step.

Figure 26:
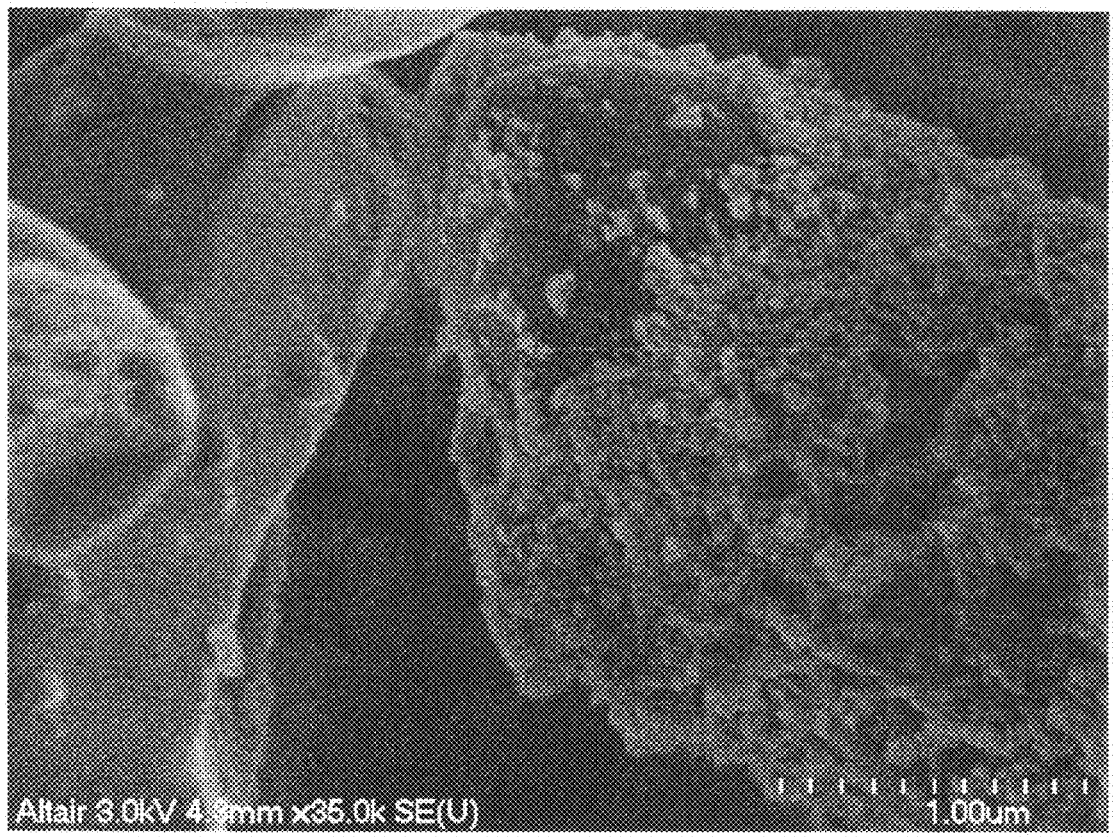
FIG. 26 is a scanning electron micrograph of a $TiO_2$ structure coated with LaOCl, made according to the process of the present invention, calcined at 600° C.
Figure 27:
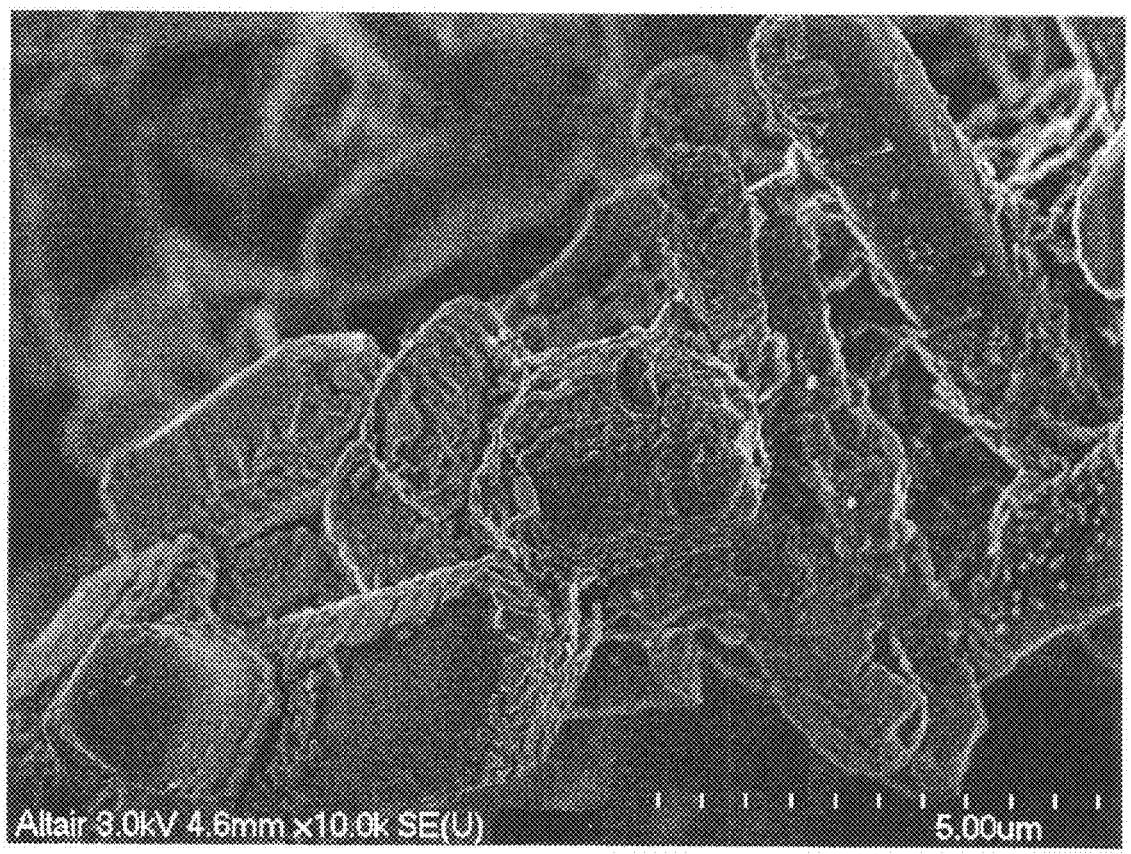
FIG. 27 is a scanning electron micrograph of a $TiO_2$ structure coated with LaOCl, made according to the process of the present invention, calcined at 900° C.
Figure 28:
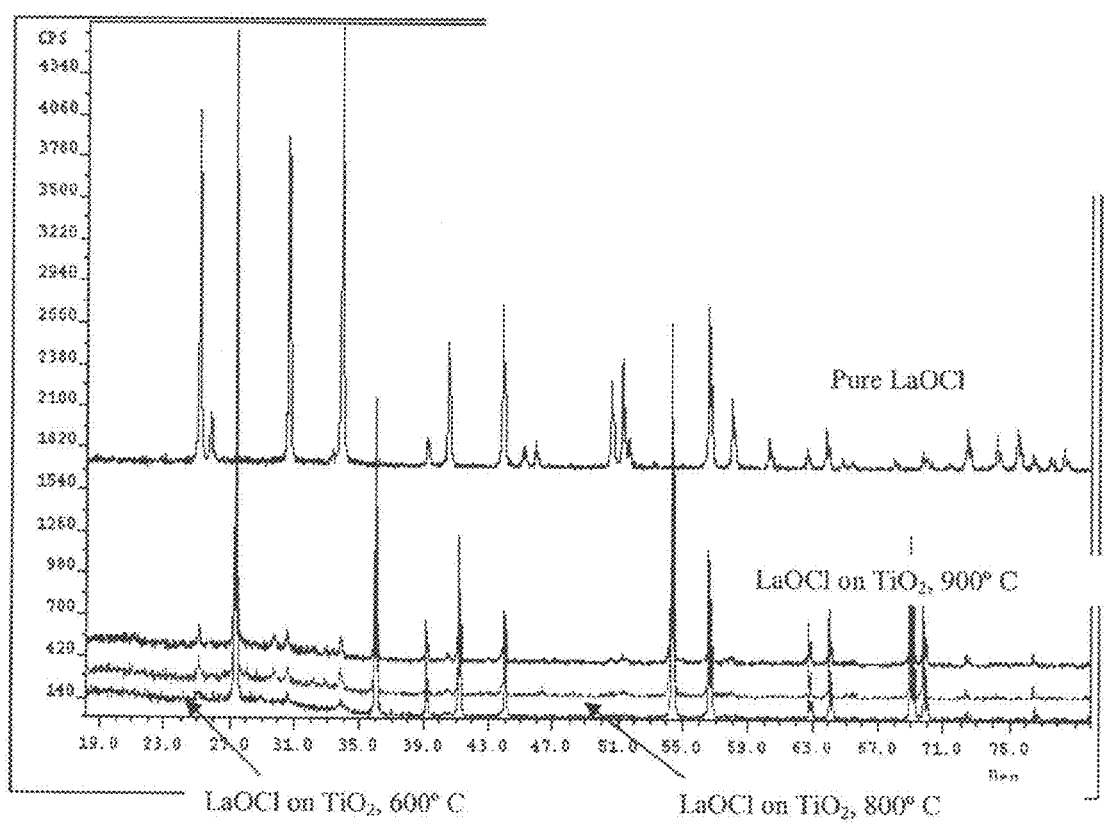
FIG. 28. shows X-Ray scans for $TiO_2$ coated with LaOCl and calcined at different temperatures following the process of the present invention, and compared to the X-Ray scan for pure LaOCl.

FIG. 26 is a scanning electron micrograph corresponding to calcination at 600° C. instead of 800° C. It shows LaOCl particles that are smaller and less well attached to the $TiO_2$ substrate. FIG. 27 is a scanning electron micrograph corresponding to calcination at 900° C. instead of 800° C. The product is similar to the product made at 800° C., but the LaOCl deposit is present as somewhat larger crystals and more compact layer coating the TiO2 support crystals. FIG. 28 shows the X-Ray diffraction patterns corresponding to calcinations at 600°, 800° and 900° C. The figure also shows the pattern corresponding to pure LaOCl. The peaks that do not appear in the pure LaOCl pattern correspond to rutile $TiO_2$. As the temperature increases, the peaks tend to become higher and narrower, showing that the crystal size of the LaOCl as well as $TiO_2$ increases with the temperature.

EXAMPLE 11

An aqueous HCl solution having a volume of 334.75 ml and containing $LaCl_3$ (lanthanum chloride) at a concentration of 29.2 wt % as $La_2O_3$ was added to a 4 liter beaker and heated to 80° C. with stirring. The initial pH of the $LaCl_3$ solution was 2.2. Two hundred and sixty five ml of an aqueous solution containing 63.59 g of sodium carbonate ($Na_2CO_3$) was metered into the heated beaker using a small pump at a steady flow rate for 2 hours. Using a Buchner filtering apparatus fitted with filter paper the filtrate was separated from the white powder product. The filter cake was mixed four times, each with 2 liters of distilled water and filtered to wash away the NaCl formed during the reaction. The washed filter cake was placed into a convection oven set at 105° C. for 2 hours or until a stable weight was observed. The X-Ray diffraction pattern of the product shows that it consists of hydrated lanthanum oxycarbonate $La_2O(CO_3)_2.xH_2O$, where $2 \leq x \leq 4$. The surface area of the product was determined by the BET method. The test was repeated 3 times and slightly different surface areas and different reaction rates were obtained as shown in Table 1.

EXAMPLE 12

Six adult beagle dogs were dosed orally with capsules of lanthanum oxycarbonate $La_2O(CO_3)_2.xH_2O$ (compound A) or $La_2O_2CO_3$ (compound B) in a cross-over design using a dose of 2250 mg elemental lanthanum twice daily (6 hours apart). The doses were administered 30 minutes after provision of food to the animals. At least 14 days washout was allowed between the crossover arms. Plasma was obtained pre-dose and 1.5, 3, 6, 7.5, 9, 12, 24, 36, 48, 60, and 72 hours after dosing and analyzed for lanthanum using ICP-MS. Urine was collected by catheterization before and approximately 24 hours after dosing and creatinine and phosphorus concentrations measured.

The tests led to reduction of urine phosphate excretion, a marker of phosphorous binding. Values of phosphate excretion in urine are shown in Table 2 below.

TABLE 2

| La Oxycarbonate compound | Median phosphorus/creatinine ratio (% reduction compared to pre-dose value) | 10th and 90th percentiles |
|---|---|---|
| A | 48.4% | 22.6-84.4% |
| B | 37.0% | −4.1-63.1% |

Figure 29:
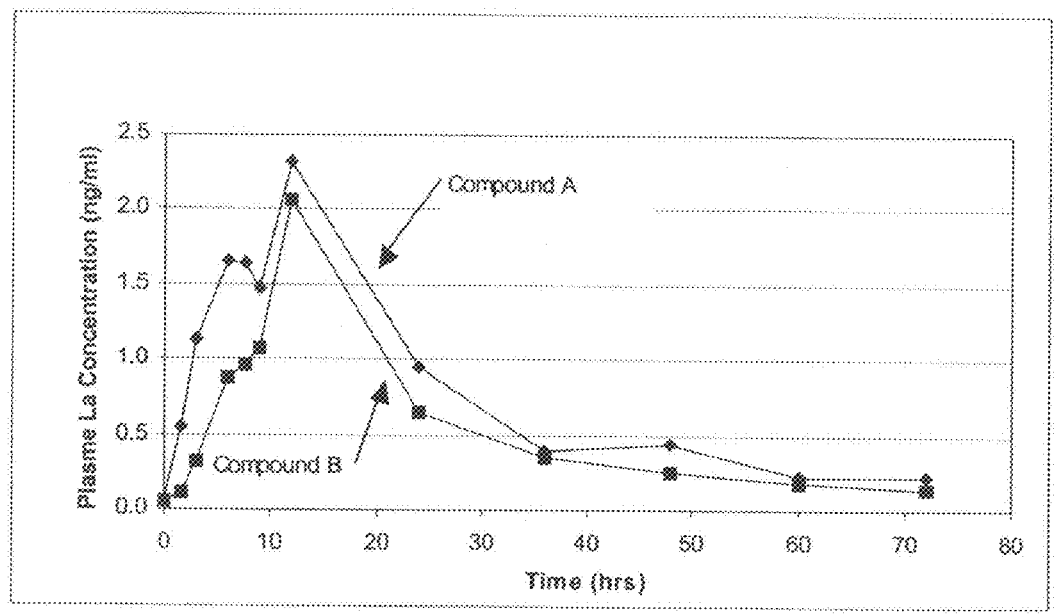
FIG. 29 shows the concentration of lanthanum in blood plasma as a function of time, for dogs treated with lanthanum oxycarbonates made according to the process of the present invention.

Plasma lanthanum exposure: Overall plasma lanthanum exposure in the dogs is summarized in Table 3 below. The plasma concentration curves are shown in FIG. 29.

TABLE 3

| La oxycarbonate compound tested | Mean (sd) Area Under the Curve$_{0-72\,h}$ (ng·h/mL); (standard deviation) | Maximum concentration $C_{max}$ (ng/mL); (standard deviation) |
|---|---|---|
| A | 54.6 (28.0) | 2.77 (2.1) |
| B | 42.7 (34.8) | 2.45 (2.2) |

EXAMPLE 13

First in vivo Study in Rats

Groups of six adult Sprague-Dawley rats underwent ⅚th nephrectomy in two stages over a period of 2 weeks and were then allowed to recover for a further two weeks prior to being randomized for treatment. The groups received vehicle (0.5% w/v carboxymethyl cellulose), or lanthanum oxycarbonate A or B suspended in vehicle, once daily for 14 days by oral lavage (10 ml/kg/day). The dose delivered 314 mg elemental lanthanum/kg/day. Dosing was carried out immediately before the dark (feeding) cycle on each day. Urine samples (24 hours) were collected prior to surgery, prior to the commencement of treatment, and twice weekly during the treatment period. Volume and phosphorus concentration were measured.

Feeding—During the acclimatization and surgery period, the animals were given Teklad phosphate sufficient diet (0.5% Ca, 0.3% P; Teklad No. TD85343), ad libitum. At the beginning of the treatment period, animals were pair fed based upon the average food consumption of the vehicle-treated animals the previous week.

⅚ Nephrectomy—After one week of acclimatization, all animals were subjected to ⅚ nephrectomy surgery. The surgery was performed in two stages. First, the two lower branches of the left renal artery were ligated. One week later, a right nephrectomy was performed. Prior to each surgery, animals were anesthetized with an intra-peritoneal injection of ketamine/xylazine mixture (Ketaject a 100 mg/ml and Xylaject at 20 mg/ml) administered at 10 ml/kg. After each surgery, 0.25 mg/kg Buprenorphine was administered for relief of post-surgical pain. After surgery, animals were allowed to stabilize for 2 weeks to beginning treatment.

Figure 30:
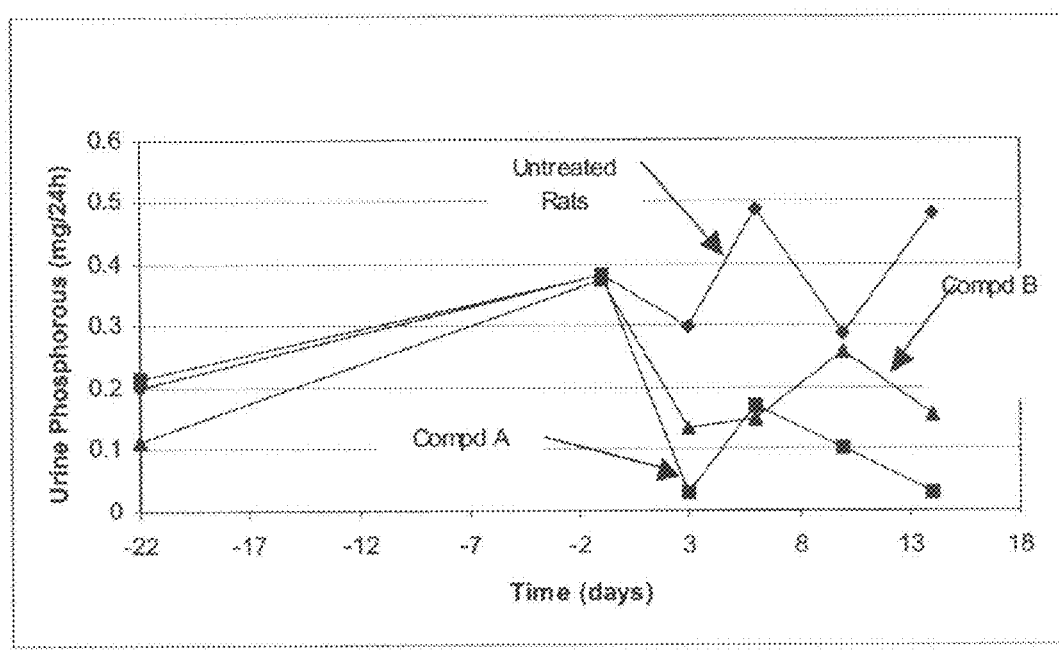
FIG. 30 shows the concentration of phosphorous in urine as a function of time in rats treated with lanthanum oxycarbonates made according to the process of the present invention, and compared to phosphorus concentration measured in untreated rats.

The results showing urine phosphorus excretion are given in FIG. 30. The results show a decrease in phosphorus excretion, a marker of dietary phosphorus binding, after administration of the lanthanum oxycarbonate (at time>0), compared to untreated rats.

EXAMPLE 14

Second in vivo Study in Rats

Six young adult male Sprague-Dawley rats were randomly assigned to each group. Test items were lanthanum oxycarbonates $La_2O_2CO_3$ and $La_2CO_5$ (compound B and compound C), each tested at 0.3 and 0.6% of diet. There was an additional negative control group receiving Sigmacell cellulose in place of the test item.

The test items were mixed thoroughly into Teklad 7012CM diet. All groups received equivalent amounts of dietary nutrients.

Table 4 outlines the dietary composition of each group:

TABLE 4

| Group ID | Treatment | Test Item | Sigmacell cellulose | Teklad Diet |
|---|---|---|---|---|
| I | Negative control | 0.0% | 1.2% | 98.8% |
| II | Compound B - Mid level | 0.3% | 0.9% | 98.8% |
| III | Compound B - High level | 0.6% | 0.6% | 98.8% |
| IV | Compound C - Mid level | 0.3% | 0.9% | 98.8% |
| V | Compound C - High level | 0.6% | 0.6% | 98.8% |

Rats were maintained in the animal facility for at least five days prior to use, housed individually in stainless steel hanging cages. On the first day of testing, they were placed individually in metabolic cages along with their test diet. Every 24 hours, their output of urine and feces was measured and collected and their general health visually assessed. The study continued for 4 days. Food consumption for each day of the study was recorded. Starting and ending animal weights were recorded.

Plasma samples were collected via retro-orbital bleeding from the control (I) and high-dose oxycarbonate groups, III and V. The rats were then euthanized with $CO_2$ in accordance with the IACUC study protocol.

Urine samples were assayed for phosphorus, calcium, and creatinine concentration in a Hitachi 912 analyzer using Roche reagents. Urinary excretion of phosphorus per day was calculated for each rat from daily urine volume and phosphorus concentration. No significant changes were seen in animal weight, urine volume or creatinine excretion between groups. Food consumption was good for all groups.

Even though lanthanum dosage was relatively low compared to the amount of phosphate in the diet, phosphate excretion for 0.3 or 0.6% La added to the diet decreased as shown in Table 5 below. Table 5 shows average levels of urinary phosphate over days 2, 3, and 4 of the test. Urine phosphorus excretion is a marker of dietary phosphorous binding.

TABLE 5

| | Urinary phosphate excretion (mg/day) |
|---|---|
| Control | 4.3 |
| Compound B = $La_2O_2CO_3$ | 2.3 |
| Compound C = $La_2CO_5$ | 1.9 |

EXAMPLE 15

Tests were run to determine the binding efficiency of eight different compounds for twenty-four different elements. The compounds tested are given in Table 6.

TABLE 6

| Test ID | Compound | Preparation Technique |
|---|---|---|
| 1 | $La_2O_3$ | Calcined the commercial (Prochem) $La_2(CO_3)_3.H_2O$ at 850° C. for 16 hrs. |
| 2 | $La_2CO_5$ | Prepared by spray drying lanthanum acetate solution and calcining at 600° C. for 7 hrs (method corresponding to FIG. 3) |
| 3 | LaOCl | Prepared by spray drying lanthanum chloride solution and calcining at 700° C. for 10 hrs (method corresponding to FIG. 1) |
| 4 | $La_2(CO_3)_3.4H_2O$ | Purchased from Prochem (comparative example) |
| 5 | Ti carbonate | Made by the method of FIG. 11, where the $LaCl_3$ solution is replaced by a $TiOCl_2$ solution. |
| 6 | $TiO_2$ | Made by the method corresponding to FIG. 2, with addition of sodium chloride. |
| 7 | $La_2O(CO_3)_2.xH_2O$ | Precipitation by adding sodium carbonate solution to lanthanum chloride solution at 80° C. (Method corresponding to FIG. 10) |
| 8 | $La_2O_2CO_3$ | Precipitation by adding sodium carbonate solution to lanthanum chloride solution at 80° C. followed by calcination at 500° C. for 3 hrs. (Method of FIG. 11) |

The main objective of the tests was to investigate the efficiency at the compounds bind arsenic and selenium, in view of their use in removing those nts from drinking water. Twenty-one different anions were also included to explore r possibilities. The tests were performed as follows:

The compounds given in Table 6 were added to water and a spike and vigorously shaken at room temperature for 18 hrs. The samples were filtered and ltrate analyzed for a suite of elements including Sb, As, Be, Cd, Ca, Cr, Co, Cu, Fe, g, Mn, Mo, Ni, Se, Tl, Ti, V, Zn, Al, Ba, B, Ag, and P.

The spike solution was made as follows:
1. In a 500 ml volumetric cylinder add 400 ml of de-ionized water.
2. Add standard solutions of the elements given above to make solutions containing approximately 1 mg/l of each element.
3. Dilute to 500 mls with de-ionized water.

The tests were conducted as follows:
1. Weigh 0.50 g of each compound into its own 50 ml centrifuge tube.
2. Add 30.0 ml of the spike solution to each.
3. Cap tightly and shake vigorously for 18 hrs.
4. Filter solution from each centrifuge tube through 0.2 μm syringe filter. Obtain ~6 ml of filtrate.
5. Dilute filtrates 5:10 with 2% $HNO_3$. Final Matrix is 1% $HNO_3$.
6. Submit for analysis.

The results of the tests are given in Table 7.

TABLE 7

% of the Analyte Removed

| | Sb | As | Be | Cd | Ca | Cr | Co | Cu | Fe | Pb | Mg | Mn |
|---|---|---|---|---|---|---|---|---|---|---|---|---|
| $La_2O_3$ | 89 | 85 | 97 | 95 | 21 | 100 | 69 | 89 | 92 | 92 | 0 | 94 |
| $La_2CO_5$ | 96 | 93 | 100 | 83 | 0 | 100 | 52 | 97 | 100 | 99 | 0 | 99 |
| LaOCl | 86 | 76 | 89 | 46 | 0 | 100 | 28 | 88 | 100 | 99 | 0 | 28 |
| $La_2(CO_3)_3.4H_2O$ | 84 | 25 | 41 | 37 | 28 | 94 | 20 | 0 | 56 | 90 | 0 | 20 |
| $Ti(CO_3)_2$ | 96 | 93 | 100 | 100 | 99 | 99 | 99 | 98 | 100 | 98 | 79 | 100 |
| $TiO_2$ | 96 | 93 | 8 | 4 | 0 | 6 | 0 | 11 | 49 | 97 | 0 | 1 |
| $La_2O(CO_3)_2.xH_2O$ | 87 | 29 | 53 | 37 | 28 | 100 | 20 | 10 | 58 | 98 | 0 | 25 |
| $La_2O_2CO_3$ | 97 | 92 | 100 | 85 | 21 | 100 | 59 | 98 | 100 | 99 | 0 | 99 |

| | Mo | Ni | Se | Tl | Ti | V | Zn | Al | Ba | B | Ag | P |
|---|---|---|---|---|---|---|---|---|---|---|---|---|
| $La_2O_3$ | 89 | 28 | 72 | 8 | 90 | 95 | 95 | 85 | 23 | 0 | 47 | 96 |
| $La_2CO_5$ | 98 | 17 | 79 | 8 | 100 | 99 | 100 | 93 | 0 | 0 | 73 | 99 |
| LaOCl | 94 | 0 | 71 | 13 | 100 | 99 | 24 | 92 | 7 | 0 | 96 | 96 |
| $La_2(CO_3)_3.4H_2O$ | 98 | 1 | 78 | 5 | 100 | 99 | 16 | 11 | 23 | 0 | 48 | 71 |
| $Ti(CO_3)_2$ | 91 | 98 | 97 | 96 | 24 | 100 | 100 | 92 | 100 | 0 | 99 | 98 |
| $TiO_2$ | 97 | 0 | 97 | 62 | 0 | 86 | 0 | 0 | 0 | 30 | 99 | 66 |
| $La_2O(CO_3)_2.xH_2O$ | 99 | 0 | 79 | 8 | 100 | 99 | 16 | 60 | 26 | 0 | 44 | 74 |
| $La_2O_2CO_3$ | 99 | 34 | 81 | 12 | 100 | 99 | 100 | 92 | 23 | 0 | 87 | 99 |

The most efficient compounds for removing both arsenic and selenium appear to be the titanium-based compounds 5 and 6. The lanthanum oxycarbonates made according to the process of the present invention remove at least 90% of the arsenic. Their efficiency at removing Se is in the range 70 to 80%. Commercial lanthanum carbonate (4 in Table 6) is less effective.

The tests show that the lanthanum and titanium compounds made following the process of the present invention are also effective at removing Sb, Cr, Pb, Mo from solution. They also confirm the efficient removal of phosphorus discussed in the previous examples.

While the invention has been described in conjunction with specific embodiments, it is to be understood that many alternatives, modifications, and variations will be apparent to those skilled in the art in light of the foregoing description. Accordingly, this invention is intended to embrace all such alternatives, modifications, and variations that fall within the spirit and scope of the appended claims.

What is claimed is:

1. A method of treating hyperphosphatemia in a mammal, wherein the method comprises administering an effective amount of a composition comprising a lanthanum compound of the formula $La_2O_2CO_3$ having a phosphate binding capacity of at least 50 mg $PO_4$/g of the lanthanum compound.

2. The method according to claim 1, wherein the lanthanum compound has a phosphate binding capacity of at least 75 mg $PO_4$/g of the lanthanum compound.

3. The method according to claim 1, wherein the lanthanum compound has a BET specific surface area of at least 10 $m^2$/g.

4. The method according to claim 1, wherein the lanthanum compound has a BET specific surface area of about 10 $m^2$/g.

5. The method according to claim 1, wherein the lanthanum compound comprises particles, and wherein the particles are between 1 and 1000 μm in size.

6. The method according to claim 5, wherein the particles comprise individual crystals.

7. The method according to claim 6, wherein the lanthanum compound has a BET specific surface area of at least 10 $m^2$/g.

8. The method according to claim 6, wherein the lanthanum compound has a BET specific surface area of about 10 $m^2$/g.

9. The method according to claim 7, wherein the lanthanum compound has a phosphate binding capacity of at least 100 mg $PO_4$/g of the lanthanum compound.

10. The method according to claim 9, wherein the individual crystals are between 20 nm and 10 μm in size.

11. The method according to claim 1, wherein the composition is formulated to provide an orally ingestible form.

12. The method according to claim 11, wherein the orally ingestible form is selected from the group consisting of liquid solution, liquid suspension, tablet, capsule, and gelcap.

* * * * *

UNITED STATES PATENT AND TRADEMARK OFFICE
CERTIFICATE OF CORRECTION

PATENT NO.       : 7,588,782 B2
APPLICATION NO.  : 11/181650
DATED            : September 15, 2009
INVENTOR(S)      : Moerck et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 784 days.

Signed and Sealed this

Twenty-first Day of September, 2010

David J. Kappos
*Director of the United States Patent and Trademark Office*